(12) United States Patent
Huizinga et al.

(10) Patent No.: US 7,674,454 B2
(45) Date of Patent: Mar. 9, 2010

(54) ENZYME-PRODRUG THERAPY FOR PROSTHETIC JOINT REPAIR

(75) Inventors: Tom J. W. Huizinga, Leiden (NL); Robert C. Hoeben, Leiden (NL); Rob G. H. H. Nelissen, Leiden (NL); Andrew Mountain, London (GB)

(73) Assignees: Innovata Limited (GB); Academisch Ziekenhuis Leiden (NL)

( * ) Notice: Subject to any disclaimer, the term of this patent is extended or adjusted under 35 U.S.C. 154(b) by 0 days.

(21) Appl. No.: 11/072,980

(22) Filed: Mar. 4, 2005

(65) Prior Publication Data

US 2005/0260160 A1 Nov. 24, 2005

Related U.S. Application Data

(60) Provisional application No. 60/563,067, filed on Apr. 16, 2004, provisional application No. 60/613,305, filed on Sep. 27, 2004.

(30) Foreign Application Priority Data

Mar. 6, 2004 (GB) ................................. 0405103.3
Sep. 11, 2004 (GB) ................................. 0420217.2

(51) Int. Cl.
A61K 48/00 (2006.01)
A61K 31/70 (2006.01)
C12N 15/63 (2006.01)
(52) U.S. Cl. ....................... 424/93.2; 514/44; 435/320.1
(58) Field of Classification Search ................. 424/93.2; 514/44; 435/320.1
See application file for complete search history.

(56) References Cited

U.S. PATENT DOCUMENTS 5,972,913 A 10/1999 Yates

FOREIGN PATENT DOCUMENTS

WO WO 96/39107 * 12/1996
WO WO 00/40271 7/2000

OTHER PUBLICATIONS

Brey et al Ann N Y Acad Sci. 1997; 823:97-106.*
Goodman & Gilman's The Pharmacological basis of Therapeutics, McGraw-Hill, New York, NY. pp. 77-101.*
Verma and Somia (1997) Nature 389:239-242.*
Pfeifer and Verma (2001) Annual Review of Genomics and Human Genetics.2: 177-211.*
Wooley et al Gene Therapy (2004) 11, 402-407.*
Filion et al Br J Pharmacol. 1997;122(3): 551-557.*
Davis et al Current Opinion in Biotechnology 2002, 13:128-131.*
Jiranek et al J Bone Joint Surg Am. 1993, 75(6):863-79).*
Jones LC et al , J Biomed Mater Res. 1999;48(6):889-98.*
McNeish et al Advanced Drug Delivery Reviews, 26, 1997, 173-184.*
Weedon SJ et al Int J Cancer. 2000, 86(6): 848-54.*
Romano G et al Stem Cells. 2000;18(1):19-39.*
Nasu et al, Mol. Urol 2000, 4(2), 67-71, abstract only.*
Stone et al Molecular Therapy (2007) 15, 2146-2153.*
Baker et al Molecular Therapy , Dec. 2007, 2061-2062.*
Lieberman J Bone Joint Surg Br. Nov. 1993;75(6):869-71.*
Childs J Bone Joint Surg Am. 2001; 83 (12):1789-97.*
Djeha et al., "Combined Adenovirus-Mediated Nitroreductase Gene Delivery and CB1954 Treatment: A Well-Tolerated Therapy for Established Solid Tumors," Mol Ther (2001) 3(2):233-240.
Gallo et al., "A Comprehensive Theory of Periprosthetic Osteolysis: A Review," Biomed Papers (2002) 146(2):21-28.
Goosens et al., "Feasibility of Adenovirus-Mediated Nonsurgical Synovectomy in Collagen-Induced Arthritis-Affected Rhesus Monkeys," Hum Gene Ther (1999) 10:1139-1149.
Grove et al., "Virus-detected enzyme prodrug therapy using C81954," Anti-Cancer Drug Design (1999) 14(6):461-472.
Knox et al., "A new cytotoxic, DNA interstrand crosslinking agent, 5-(aziridin-1-yl)-4- hydroxylamino-2-nitrobenzamide, is formed from 5-(aziridin-1-yl)-2,4-dinitrobenzamide (CB 1954) by a nitroreductase enzyme in Walker carcinoma cells," Biochemical Pharmacology (1988) 37(24):4661-4669.
Knox et al., "Bioactivation of CB 1954: Reaction of the active 4-hydroxylamino derivative with thioesters to form the ultimate DNA-DNA interstrand crosslinking species," Biochem Pharmacology (1991) 42(9):1691-1697.
McNeish et al., "Virus directed enzyme prodrug therapy for ovarian and pancreatic cancer using retrovirally delivered E. coli nitroreductase and CB1954," Gene Ther (1998) 5(8):1061-1069.
Moolten et al., "Tumor chemosensitivity conferred by inserted herpes thymidine kinase genes: paradigm for a prospective cancer control strategy," Cancer Res (1986) 46(10):5276-5281.
Motyckova et al., "Linking osteopetrosis and pycnodysostosis: regulation of cathepsin K expression by the microphthalmia transcription factor family," Proc Natl Acad Sci USA (2001) 98(10):5798-5803.
Mullen et al., "Transfer of the bacterial gene for cytosine deaminase to mammalian cells confers lethal sensitivity to 5-fluorocytosine: a negative selection system," PNAS USA (1992) 89(1):33-37.
Ulrich et al., "Recombinant adeno-associated virus-mediated osteoprotegerin gene therapy," J Bone Joint Surg (2002) 84A:1405-1412.
Schwarz et al., "Anti-TNF-alpha therapy as a clinical intervention for periprosthetic osteolysis," Arthritis Research (2000) 2(3):165-168.
Total Hip Replacement. NIH Consensus Statement Online Sep. 12-14, 1994; 12(1):1-31.
Xu et al., "Strategies for enzyme/prodrug cancer therapy," Clinical Cancer Research (2001) 7(11):3314-3324.
Knox, Richard J., Et Al., The Nitroreductase Enzyme in Walker Cells that Activates 5-(Aziridin-1-Yl)-4- Hydroxylamino-2-Nitrobenzamide is a form of Nad(P)H Dehydrogenase (Quinone) (EC 1.6.99.2), Biochemical Pharmacology, vol. 37, No. 24 pp. 4671-4677, 1988.

* cited by examiner

Primary Examiner—Deborah Crouch
Assistant Examiner—Anoop Singh
(74) Attorney, Agent, or Firm—Cozen O'Connor

(57) ABSTRACT

The invention relates to the use of gene therapy in the treatment of aseptic loosening of orthopaedic prostheses and discloses methods of refixing such prostheses without open revision surgery. In particular, it provides adenoviral vectors and prodrugs for simultaneous, separate or sequential use in the destruction of interface tissue allowing subsequent recementing of loose prostheses in a minimally invasive manner.

2 Claims, 9 Drawing Sheets

A

B

C

A

B

ENZYME-PRODRUG THERAPY FOR PROSTHETIC JOINT REPAIR

CROSS REFERENCE TO RELATED APPLICATIONS

The present application claims priority under 35 U.S.C. § 119(e) Provisional Application Ser. No. 60/563,067, Filed: Apr. 16, 2004 and Provisional Application Ser. No. 60/613,305, Filed: Sep. 27, 2004 and claims priority under 35 U.S.C. § 119(a) to Great Britain Patent Application No. 0405103.3, Filed: 6 Mar. 2004 and Great Britain Patent Application No. 0420217.2, Filed: 11 Sep. 2004. All applications are hereby incorporated by reference in their entireties.

FIELD OF THE INVENTION

The invention relates to the use of gene therapy in the treatment of aseptic loosening of orthopaedic prostheses. In particular, it discloses methods of refixing such prostheses without open revision surgery.

BACKGROUND TO THE INVENTION

Approximately 1 million total hip replacement (total hip arthroplasty) operations are carried out world-wide annually, with more than 120,000 of these undertaken in the USA, and about 35,000 in England alone (NIH Consensus Statement, 1994; NHS Review 1996). This is likely to increase to approximately 3 million worldwide per annum within the next decade. Hip replacements are very often performed in elderly patients and, amongst this group, loosening of one or both components of the prosthesis, resulting in severe mobility restriction, occurs within 15 years in about a third of patients. Where prosthetic loosening occurs, patients' experience increased pain and walking difficulty and have a higher risk of dislocations and pathological fractures. Within 10 years, approximately 10% of all patients require revision surgery, which has a high rate of complications and failure (Hellman et al, 1999).

The most common cause of implant failure is aseptic loosening as a result of particulate-induced osteolysis. Wear particles, such as particles of polyethylene, polymethylmethacrylate, titanium, cobalt chrome or ceramic debris, depending on the type of prosthesis, stimulate an inflammatory response termed periprosthetic osteolysis (Goldring et al, 1986). The phagocytosis of wear particles by macrophages activates them, leading to secretion of the inflammatory cytokines IL-1, TNF-α, and IL-6. The resulting chronic inflammatory response eventually produces a pseudomembrane of granulomatous 'interface tissue' including activated macrophages, fibroblasts, giant cells and osteoclasts, similar to the pannus characteristic of arthritic joints. The end result of this complex inflammatory and proliferative foreign body response is osteoclast-mediated resorption of bone, leading to loosening of one or both components of the prosthetic implant. Prostheses for total hip arthroplasty consist of two components. An artificial socket, or acetabular component, is located in a prepared cavity in the acetabulum of the pelvis. This articulates with a femoral component comprising a ball attached to a process, which is introduced into a prepared cavity in the medulla of the femur. Many variations of both components exist, and they may be retained with or without cements.

Aseptic loosening eventually leads to an unacceptable degree of pain, immobility or walking difficulties and instability, with a higher risk of dislocations and pathological fractures. In some patients revision surgery may be undertaken to remove the inflammatory tissue and replace the prosthesis. However, revision surgery is very expensive and has a high morbidity and mortality rate, especially in elderly patients (who are in the majority). In patients with cardiac insufficiency revision surgery often has major complications such as myocardial failure or coronary artery disease (Strehle et al, 2000). Many patients are not eligible for revision surgery because the risk of mortality is considered to be too high. There is no alternative treatment for such patients, who are then wheelchair-bound. The clinical need for a less traumatic alternative to revision surgery for treatment of loosened prostheses is therefore clear. At present experimental approaches to this problem are preventative rather than therapeutic. One such preventative approach to controlling aseptic loosening involves the use of bisphosphonate compounds, especially alendronate, as either a systemic medication or as a component of a cement used to fix such prostheses (U.S. Pat. No. 5,972,913, WO 96/39107, Shanbhag et al, 1997, Leung et al, 1999). However, although bisphosphonates are known to produce an increase in skeletal bone density, they have not been shown to have a significant effect in treating rheumatoid arthritis, which shares many similar pathological features with periprosthetic osteolysis, nor on periprosthetic osteolysis itself (Ralston et al, 1989; Eggelmeijer et al, 1996; Ulrich-Vinther, 2002). It thus remains to be seen whether bisphosphonates have a useful role to play in the prevention of aseptic loosening.

In an attempt to prevent osteoclast-mediated periprosthetic bone resorption directly, an alternative preventative approach involves gene therapy (reviewed in Wooley and Schwarz, 2004), using an osteoclast inhibitory protein, osteoprotegerin, delivered by means of adeno-associated virus vector has been described (Ulrich-Vinther, 2002). Osteoprotegerin is a competitive inhibitor of an osteoclast differentiation factor, receptor activator of nuclear factor κB ligand (RANKL), which binds to a receptor expressed on the surface of macrophage-derived osteoclast precursor cells, known as receptor activator of nuclear factor κB (RANK). RANKL is secreted by osteoblasts, stromal cells and activated T cells at an early stage of the inflammatory response initiated by macrophage phagocytosis of wear particles (Teitelbaum, 2000). Binding of RANKL to RANK leads to activation of osteoclast precursor cells, differentiation, and stimulation of bone resorption. Binding of RANK by osteoprotegerin fails to activate the osteoclast precursor cells with the result that osteoprotegerin competitively inhibits RANKL.

Ulrich-Vinther et al used a recombinant adeno-associated virus (rAAV) vector to express osteoprotegerin and inhibit titanium particle-induced resorption in a mouse calvarial resorption model. Titanium particles were implanted on the calvaria (bones of the vault of the skull) and the vector administered by intramuscular injection into the quadriceps. The inhibitory effect of the osteoprotegerin was therefore systemic, with detectable increases in serum levels, and this appeared to be successful in inhibiting the experimental titanium-induced osteoclastogenesis and bone resorption seen in the untreated controls. Although interesting, it remains to be seen whether this model will form the basis of a viable preventative for clinical periprosthetic osteolysis. Even if effective, it is unclear what long-term systemic effects prolonged elevations in serum osteoprotegerin levels might have. For example, such a strategy would need to demonstrate a lack of deleterious effects on normal osteoclast function in bone remodelling.

There remains a need for effective treatments for the common and debilitating condition of periprosthetic osteolysis and its resultant aseptic loosening.

One approach to preferentially killing pathological cells, most widely used for treating cancer, is to introduce a gene into the target cells that encodes an enzyme capable of converting a prodrug of relatively low toxicity into a potent cytotoxic drug. Systemic administration of the prodrug is then tolerated since it is only converted into the toxic derivative locally, for example in a tumour, by cells expressing the prodrug-converting enzyme. This approach is known as gene-directed enzyme prodrug therapy (GDEPT), or when the gene is delivered by means of a recombinant viral vector, virus-directed prodrug therapy (VDEPT) (McNeish et al, 1997).

An example of an enzyme/prodrug system is nitroreductase and the aziridinyl prodrug CB1954 (5-(aziridin-1-yl)-2, 4-dinitrobenzamide) (Knox et al 1988). Following the observation that the Walker rat carcinoma cell line was particularly sensitive to CB1954, it was shown that this was due to the expression of the rat nitroreductase DT diaphorase. However, since CB1954 is a poor substrate for the human form of this enzyme, human tumour cells are far less sensitive to CB1954. GDEPT was conceived as a way of introducing a suitable nitroreductase, preferably with greater activity against CB1954, in order to sensitise targeted cells. The *Escherichia coli* nitroreductase (EC1.6.99.7, alternatively known as the oxygen-insensitive NAD(P)H nitroreductase or dihydropteridine reductase, and often abbreviated to NTR) encoded by the NFSB gene (alternatively known as NFNB, NFSI, or DPRA) has been widely used for this purpose (Reviewed in Grove et al, 1999). The NFSB-encoded nitroreductase (NTR) is a homodimer that binds two flavin mononucleotide (FMN) cofactor molecules. Using NADH or NADPH as an electron donor, and bound FMN as a reduced intermediate, NTR reduces one or other of the two nitro-groups of CB 1954 to give either the highly toxic 4-hydroxylamine derivative or the relatively non-toxic 2-hydroxylamine. Within cells, 5-(aziridin-1-yl)-4-hydroxylamino-2-nitrobenzamide, probably via a further toxic metabolite, becomes very genotoxic (Knox et al, 1991). The exact nature of the lesion caused is unclear, but is unlike that caused by other agents. A particularly high rate of inter-strand cross-linking occurs and the lesions seem to be poorly repaired, with the result that CB1954 is an exceptionally affective anti-tumour agent (Friedlos et al, 1992).

The aim of GDEPT is to obtain efficient conversion of a prodrug such as CB1954 in target cells in order to kill not only NTR-expressing cells but also bystander tumour cells that may not have been successfully transfected or transduced.

Another enzyme-prodrug system used in this way is that of a cytochrome P450 as a prodrug-converting enzyme and acetaminophen as the prodrug, as described in international application WO 00/40271 (incorporated herein in its entirety). A number of cytochrome P450 enzymes, naturally expressed in the liver (for example CYP1A2, CYP 2E1 and CYP3A4) are capable of converting acetaminophen into a highly cytotoxic metabolite, N-acetylbenzoquinoneimine (NABQI). This system has been proposed for a variety of clinical applications, especially in the field of cancer therapy. Cytochrome P450 enzymes are also capable of activating several conventional cytotoxic prodrugs, for example cyclophosphamide and ifosfamide (Chen and Waxman, 2002).

A number of other enzyme-prodrug systems are widely used, including HSV thymidine kinase and ganciclovir (Moolten, 1986), cytosine deaminase and 5-fluorocytosine (Mullen et al., 1992).

Goossens et al (1999) describe a viral gene therapy approach to infect and kill isolated cultured synovial cells in vitro, and to kill pannus tissue in a monkey collagen-induced arthritis model in which inflamed joints are induced by collagen injections. Inflamed joints in such animals contain a hyperplastic tissue resulting from the chronic inflammation termed pannus.

SUMMARY OF THE INVENTION

As used herein:

"Cell-type selective" means; facilitating expression preferentially in a limited range of tissues. Preferably, such expression is substantially limited to a single tissue or cell type.

An "operably-linked promoter" is one in a substantially adjacent cis-relationship, wherein said promoter directs expression of the operably-linked element.

"Periprosthetic" relates to the space surrounding any part of an implanted prosthesis "Periprosthetic osteolysis" is synonymous with "aseptic loosening" and relates to any progressive loosening of an implanted prosthesis not associated with frank infection or trauma.

"Interface tissue" is synonymous with "osteolytic membrane" and means inflammatory tissue in the periprosthetic space round an implanted prosthesis, implicated in periprosthetic osteolysis.

"Prosthesis" or "Orthopaedic implant" as herein used means any material or device surgically implanted into a bony structure of an animal or human.

An aim of the invention is to provide a non-surgical alternative to revision surgery for treatment of loosened prostheses that destroys interface tissue (and the cells within it that are involved in the inflammatory processes and bone resorption) and allows the implant to be recemented.

The invention seeks to achieve this by using an enzyme-prodrug therapy strategy using a gene therapy vector to deliver a prodrug-converting enzyme to cells in the interface tissue, thus sensitising them to a particular prodrug. Administration of the prodrug leads to its conversion to an active cytotoxic drug in the target cells, killing the interface tissue. Release of active cytotoxic drug from lysed interface cells may also kill neighbouring interface or inflammatory cells ('bystander' killing), which is advantageous in that cells that have escaped direct vector delivery (by transduction, for viral vectors, or transfection for non-viral vectors) are also eliminated.

In one strategy, a viral vector carrying nucleic acid encoding the enzyme is injected into the intra-articular space, and the prodrug subsequently administered through a small drill hole, which can also be used to inject cement to refix the prosthesis in situ. Alternatively, the prodrug may be administered by intra-articular injection. Arthrography has shown that the interface tissue forms a continuous closed compartment around the loosened prosthesis, which allows a high local concentration of both vector and prodrug to be achieved with very low risk of systemic escape. The concept thus offers more favourable circumstances in terms of both efficacy and safety than intra-tumoral injection in cancer patients, a procedure with which there is considerable clinical experience. In the case at least of adenoviral vectors, it may be preferable to remove existing fluid in the intra-articular/periprosthetic space before introducing the vectors, to reduce the possibility of neutralizing antibodies in the fluid inactivating the vector and preventing satisfactory levels of transduction.

Preferably, following introduction of the prodrug and consequent killing of cells of the interface tissue, said tissue is removed. This may be aided by the introduction of, either simultaneous with, or subsequent to, introduction of the prodrug, one or more enzymes capable of digesting extracellular components of the interface tissue, such as collagenase, elastase or hyaluronidase, matrix metalloproteases or cathepsins.

Other compounds useful for this purpose include the chelating agents EDTA (Ethylenediamine-N,N,N',N'-tetraacetic acid) and EGTA (Ethylene glycol-bis-(2-aminoethyl)-N,N,N',N'-tetraacetic acid). Such treatment digests and loosens the interface tissue, such that it may be flushed out through a suitable drill hole or via a wide bore needle introduced into the intra-articular space.

The fully loosened and debrided implant is then recemented, to solidly reattach all loosened components and restore a fully functional prosthetic joint.

Alternatively, especially with prodrugs such as acetaminophen with very low systemic toxicity, the vector encoding the prodrug converting enzyme (such as cytochrome P450) may be injected locally, so that only cells within the interface tissue/joint compartment are transduced, whilst the prodrug is subsequently administered systemically.

In one aspect of the invention, the approach is to kill cells resident in the interface tissue, irrespective of their type. In practice, the predominant cells are fibroblasts responsible for producing the extracellular matrix proteins of which much of the tissue is comprised, and cells of the monocyte/macrophage lineage responsible for inflammatory effects. In this case, the expression of the enzyme encoded by the vector is controlled by a strong non-cell type specific promoter, providing high level expression in a variety of cell and tissue types, such as the cytomegalovirus early/immediate promoter and the cytotoxic effect is limited to cells of the interface tissue by the physical constraints of the space into which the vector and/or prodrug are injected. The normal cells of most concern from the safety viewpoint are the osteoblasts responsible for bone regeneration. In most instances, and with most gene delivery vectors, these cells are inaccessible to vector injected into the periprosthetic space, hence are not transduced or transfected, do not express the prodrug converting enzyme even with a non-cell type specific promoter, and are therefore not killed upon subsequent administration of the prodrug.

Examples of such non-cell specific promoters include: cytomegalovirus immediate/early promoter, Rous sarcoma virus long terminal repeat (RSV LTR), murine leukaemia virus LTR, simian virus 40 (SV40) early or late promoters, herpes simplex virus (HSV) thymidine kinase (tk) promoter, actin or ubiquitin promoters.

In some circumstances it may be advantageous to achieve more selective cell killing, in which case the enzyme encoded by the vector may be expressed under the control of a tissue- or cell type-selective promoter. Use of such a promoter permits selective killing of cells of particular lineages, such as fibroblasts, cells of the monocyte/macrophage lineage or, more specifically, cells of a particular phenotype, such as osteoclast precursor cells, or fully differentiated osteoclasts.

Examples of promoters suitable for preferentially expressing a gene, such as a gene encoding a prodrug-converting enzyme, in cells of the monocyte/macrophage lineage include, c-fes and CD68. Promoters characterised by containing one or more binding sites for the transcription factor PU.1 are generally suitable (Greaves and Gordon, 2002).

Promoters suitable for expressing a gene preferentially in osteoclasts or osteoclast precursors include the tartrate-resistant acid phosphatase (TRAP) promoter, the RANK promoter and the cathepsin K promoter. Promoters characterised by containing one or more binding sites (E-boxes, containing the consensus binding sequences 5'-CA(T/G)GTG for microphthalmia transcription factor family (MITF, TFE3, TFEB and TFEC), optionally also containing binding sites for the transcription factor PU.1 are generally suitable (Motyckova et al, 2001; Mansky et al, 2002, Greaves and Gordon, 2002).

By the use of such specific promoters, expression of the enzyme may be restricted to particular target cells, such as those responsible for laying down of extracellular matrix proteins such as collagen (fibroblasts), those responsible for secreting inflammatory cytokines (such as macrophages) or those responsible directly for bone resorption (osteoclasts), whilst protecting other cell types (such as osteoblasts, responsible for depositing new bone).

The various possible combinations of local administration of vector and/or prodrug with or without tissue-selective expression allow non-surgical treatment of loosened prostheses and recementation of the implant, overcoming limitations in the prior art methods aimed at preventing periprosthetic loosening by systemic administration of compounds such as bisphosphonates, or of systemic expression of highly bioactive molecules such as osteoprotegerin.

Accordingly, the invention provides an isolated polynucleotide encoding an enzyme capable of converting a prodrug into an active cytotoxic compound, expression of the enzyme being controlled by an operably-linked promoter that gives substantially cell type-selective expression. Preferably expression is restricted to cells of the monocyte/macrophage lineage. Preferred examples such promoters include the promoters of such genes as c-fes, and CD68. Promoters characterised by containing one or more binding sites for the transcription factor PU.1 are generally suitable.

Alternatively, expression is restricted to fibroblasts.

More preferably expression is restricted to osteoclasts or osteoclast precursors. Amongst suitable promoters providing such expression are those naturally functionally linked to genes such as tartrate-resistant acid phosphatase (TRAP), receptor activator of nuclear factor κB (RANK) and cathepsin K. Promoters characterised by containing one or more binding sites (E-boxes, containing the consensus binding sequences 5'-CA(T/G)GTG) for microphthalmia transcription factor family (MITF, TFE3, TFEB and TFEC), optionally also containing binding sites for the transcription factor PU.1 are generally suitable.

Preferably, the enzyme encoded is a nitroreductase, preferably a nitroreductase suitable for the activation of the prodrug CB1954 (5-(aziridin-1-yl)-2,4-dinitrobenzamide). Alternatively, it a cytochrome P450. Other suitable enzyme/prodrug systems include HSV thymidine kinase and ganciclovir (Moolten, 1986), cytosine deaminase and 5-fluorocytosine (Mullen et al, 1992).

In another aspect, the invention provides a vector comprising said polynucleotide. The vector may be any vector capable of transferring DNA to a cell. Preferably, the vector is an integrating vector or an episomal vector.

Preferred integrating vectors include recombinant retroviral vectors. A recombinant retroviral vector will include DNA of at least a portion of a retroviral genome which portion is capable of infecting the target cells. The term "infection" is used to mean the process by which a virus transfers genetic material to its host or target cell. Preferably, the retrovirus used in the construction of a vector of the invention is also rendered replication-defective to remove the effect of viral replication on the target cells. In such cases, the replication-defective viral genome can be packaged by a helper virus in accordance with conventional techniques. Generally, any retrovirus meeting the above criteria of infectivity and capability of functional gene transfer can be employed in the practice of the invention. Lentiviral vectors are especially preferred.

Suitable retroviral vectors include but are not limited to pLJ, pZip, pWe and pEM, well known to those of skill in the art. Suitable packaging virus lines for replication-defective retroviruses include, for example, ΨCrip, ΨCre, Ψ2 and ΨAm.

Other vectors useful in the present invention include adenovirus, adeno-associated virus, SV40 virus, vaccinia virus, HSV and poxvirus vectors. A preferred episomal vector is the adenovirus. Adenovirus vectors are well known to those skilled in the art and have been used to deliver genes to numerous cell types, including airway epithelium, skeletal muscle, liver, brain and skin (Hitt et al, 1997; Anderson, 1998).

A further preferred vector is the adeno-associated (MV) vector. MV vectors are well known to those skilled in the art and have been used to stably transduce human T-lymphocytes, fibroblasts, nasal polyp, skeletal muscle, brain, erythroid and haematopoietic stem cells for gene therapy applications (Philip et al., 1994; Russell et al., 1994; Flotte et al., 1993; Walsh et al., 1994; Miller et al., 1994; Emerson, 1996). International Patent Application WO 91/18088 describes specific MV based vectors.

Other preferred episomal vectors include transient non-replicating episomal vectors and self-replicating episomal vectors with functions derived from viral origins of replication such as those from EBV, human papovavirus (BK) and BPV-1. Such integrating and episomal vectors are well known to those skilled in the art and are fully described in the body of literature well known to those skilled in the art. In particular, suitable episomal vectors are described in WO98/07876.

Mammalian artificial chromosomes can also be used as vectors in the present invention. The use of mammalian artificial chromosomes is discussed by Calos (1996).

In a further preferred embodiment, the vector of the present invention is a plasmid. The plasmid may be a non-replicating, non-integrating plasmid.

The term "plasmid" as used herein refers to any nucleic acid encoding an expressible gene and includes linear or circular nucleic acids and double or single stranded nucleic acids. The nucleic acid can be DNA or RNA and may comprise modified nucleotides or ribonucleotides, and may be chemically modified by such means as methylation or the inclusion of protecting groups or cap- or tail structures.

A non-replicating, non-integrating plasmid is a nucleic acid which when transfected into a host cell does not replicate and does not specifically integrate into the host cell's genome (i.e. does not integrate at high frequencies and does not integrate at specific sites).

Replicating plasmids can be identified using standard assays including the standard replication assay of Ustav and Stenlund (1991).

The present invention also provides a host cell transfected with the isolated polynucleotide or vector comprising such a polynucleotide of the present invention. The host cell may be any eukaryotic cell. Preferably it is a mammalian cell. More preferably, it is a human cell and, most preferably, it is an autologous cell derived from the patient and transfected or transduced either in vivo or ex vivo.

Numerous techniques are known and are useful according to the invention for delivering the vectors described herein to cells, including the use of nucleic acid condensing agents, electroporation, complexing with asbestos, polybrene, DEAE cellulose, Dextran, liposomes, cationic liposomes, lipopolyamines, polyornithine, particle bombardment and direct microinjection (reviewed by Kucherlapati and Skoultchi, 1984; Keown et al., 1990; Weir, 1999; Nishikawa and Huang, 2001).

A vector of the invention may be delivered to a host cell non-specifically or specifically (i.e., to a designated subset of host cells) via a viral or non-viral means of delivery. Preferred delivery methods of viral origin include viral particle-producing packaging cell lines as transfection recipients for the vector of the present invention into which viral packaging signals have been engineered, such as those of adenovirus, herpes viruses and papovaviruses. Preferred non-viral based gene delivery means and methods may also be used in the invention and include direct naked nucleic acid injection, nucleic acid condensing peptides and non-peptides, cationic liposomes and encapsulation in liposomes.

The direct delivery of vector into tissue has been described and some, mostly short-term, gene expression has been achieved. Direct delivery of vector into thyroid (Sikes et al., 1994) melanoma (Vile et al., 1993), skin (Hengge et al., 1995), liver (Hickman et al., 1994) and after exposure of airway epithelium (Meyer et al, 1995) is clearly described in the prior art. Direct DNA injection into muscle has been shown to give longer-term expression (Wolff et al., 1990).

Various peptides derived from the amino acid sequences of viral envelope proteins have been used in gene transfer when co-administered with polylysine DNA complexes (Plank et al., 1994; Trubetskoy et al., 1992; WO 91/17773; WO 92/19287) and Mack et al., (1994) suggest that co-condensation of polylysine conjugates with cationic lipids can lead to improvement in gene transfer efficiency. International Patent Application WO 95/02698 discloses the use of viral components to attempt to increase the efficiency of cationic lipid gene transfer.

Nucleic acid condensing agents useful in the invention include spermine, spermine derivatives, histones, cationic peptides, cationic non-peptides such as polyethyleneimine (PEI) and polylysine. 'Spermine derivatives' refers to analogues and derivatives of spermine and include compounds as set forth in International Patent Application WO 93/18759 (published Sep. 30, 1993).

Disulphide bonds have been used to link the peptidic components of a delivery vehicle (Cotten et al., 1992); see also Trubetskoy et al. (supra).

Delivery vehicles for delivery of DNA constructs to cells are known in the art and include DNA/poly-cation complexes which are specific for a cell surface receptor, as described in, for example, Wu and Wu, 1988; Wilson et al., 1992; and U.S. Pat. No. 5,166,320.

Delivery of a vector according to the invention is contemplated using nucleic acid condensing peptides. Nucleic acid condensing peptides, which are particularly useful for condensing the vector and delivering the vector to a cell, are described in International Patent Application WO 96/41606. Functional groups may be bound to peptides useful for delivery of a vector according to the invention, as described in WO 96/41606. These functional groups may include a ligand that targets a specific cell-type such as a monoclonal antibody, insulin, transferrin, asialoglycoprotein, or a sugar. The ligand thus may target cells in a non-specific manner or in a specific manner that is restricted with respect to cell type.

The functional groups also may comprise a lipid, such as palmitoyl, oleyl, or stearoyl; a neutral hydrophilic polymer such as polyethylene glycol (PEG), or polyvinylpyrrolidine (PVP); a fusogenic peptide such as the HA peptide of influenza virus; or a recombinase or an integrase. The functional group also may comprise an intracellular trafficking protein such as a nuclear localisation sequence (NLS), an endosome escape signal such as a membrane disruptive peptide, or a signal directing a protein directly to the cytoplasm.

The invention provides a pharmaceutical composition comprising the isolated polynucleotide, vector or host cell of the invention as described, and a pharmaceutically acceptable excipient, carrier, diluent or buffer.

In another aspect, the invention provides a product comprising a combination of the isolated polynucleotide, vector or host cell of the invention as described, and a prodrug capable of being converted into an active cytotoxic compound by the enzyme encoded by said nucleotide or vector, or expressed by the host cell, as a combined medicament for simultaneous, separate or sequential use in the treatment of aseptic loosening of orthopaedic implants, such as prostheses used for total hip arthroplasty. The loosening may be of the acetabular component or the femoral component, or both. The invention is not restricted to prostheses of the hip, but may be applied to any intraosseous implant where aseptic loosening may occur. Accordingly its use for prostheses used in arthroplasty of the knee, elbow, shoulder, or any other joint of the skeleton is specifically envisaged.

Such use need not be restricted to human use. The method is equally applicable to loosening of prostheses of animal joints, in particular horses and dogs.

Preferably, the enzyme of such a product is a nitroreductase, more preferably a nitroreductase suitable for activation of CB1954. Most preferably, the prodrug is CB1954.

Alternatively, the enzyme is a cytochrome P450 of a type herein described. Most preferably the prodrug is acetaminophen.

In a further aspect of the invention, the use of a product comprising a combination of at least one vector, which comprises an isolated polynucleotide encoding an enzyme capable of converting a prodrug into an active cytotoxic compound, expression of the enzyme being controlled by an operably-linked promoter; and a prodrug capable of being converted into an active cytotoxic compound by said enzyme, for the manufacture of a combined medicament for simultaneous, separate or sequential use in the treatment of aseptic loosening of orthopaedic implants is provided.

The promoter controlling expression of the prodrug-converting enzyme may be a non-cell type specific promoter. Preferably, said promoter gives high levels of expression in a variety of tissues and cell types. More preferably it is selected from at least one of the following; the CMV immediate/early promoter, RSV LTR), murine leukaemia virus LTR, SV40 early or late promoters, HSV tk promoter. In a further preferred embodiment it is the human cytomegalovirus immediate/early promoter. Alternatively, it is the mouse cytomegalovirus immediate/early promoter.

In an alternative preferred product for use in the manufacture of a combined medicament for simultaneous, separate or sequential use in the treatment of aseptic loosening of orthopaedic implants, expression of the enzyme is controlled by an operably-linked promoter, which provides substantially cell-type specific expression. More preferably expression is restricted to cells of the monocyte/macrophage lineage or fibroblasts, in which case the promoter may be naturally linked to a gene selectively expressed in cells of one of these lineages, as described above.

Most preferably expression is restricted to osteoclasts or osteoclast precursors, as described above.

Preferably, the enzyme is a nitroreductase, and most preferably a nitroreductase suitable for activating CB1954. In this case it is preferred that the prodrug is CB1954.

Alternatively, the enzyme may be a cytochrome P450 as herein described. In this case it is preferred that the prodrug is acetaminophen. Alternatively, it may be a conventional cytotoxic, especially cyclophosphamide or ifosfamide.

A further aspect of the invention provides a method of treating aseptic loosening of orthopaedic implants comprising administering to a patient a vector encoding an enzyme capable of converting a prodrug into an active cytotoxic compound, allowing the expression of said enzyme in target cells, and administering a suitable prodrug.

As will be appreciated by those of skill in the art, dosages are determined by clearly understood clinical parameters. However, it is preferred that the viral dose per joint treated is between $10^5$ and $10^{12}$ pfu, more preferably between $10^6$ and $10^{12}$ pfu, further preferably between $10^7$ and $10^{12}$ pfu and most preferably between $10^9$ and $10^{12}$ pfu. Similarly, the dose of prodrug is dependent on clinical parameters. In the case of CB1954, it is preferred that the dose should be between 5 and 40 mg m$^{-2}$, preferably between 5 and 30 mg m$^{-2}$, further preferably between 10 and 25 mg m$^{-2}$, more preferably between 15 and 25 mg m$^{-2}$, and most preferably 24 mg m$^{-2}$ given by intra-articular injection.

It is preferred that viral vectors are not co-administered with an iodine-containing contrast medium, since such media can inhibit viral transduction of target cells. Where the injection is to be directed by with arthroscopic visualisation, it is preferred that an air arthrogram is performed, or a contrast medium that does not inhibit viral transduction is used.

Preferably, the vector is administered by intra-articular or periprosthetic injection.

It is also preferred that the prodrug is administered by intra-articular or periprosthetic injection. Alternatively, the prodrug may be administered systemically, more preferably parenterally. However some prodrugs, particularly acetaminophen, may be administered orally.

In one preferred embodiment, expression of the prodrug-converting enzyme is controlled by a promoter that provides non-cell type specific expression. In this case expression is not restricted to a particular tissue or cell type. As described herein, it is preferred that such promoters give high levels of expression in a variety of cell types. Examples of suitable promoters include the cytomegalovirus immediate/early promoter, Rous sarcoma virus long terminal repeat (RSV LTR), murine leukaemia virus LTR, simian virus 40 (SV40) early or late promoters, herpes simplex virus (HSV) thymidine kinase (tk) promoter In an alternative preferred embodiment, expression of the prodrug converting enzyme is controlled by a promoter that provides substantially cell-type specific expression. Preferably, this is substantially restricted to cells of the monocyte/macrophage lineage. Suitable promoters are described herein. Alternatively, it is restricted to expression in fibroblasts. More preferably, it is substantially restricted to osteoclasts or osteoclast precursors. Suitable and preferred promoters include the TRAP, RANK, and cathepsin K promoters.

As herein described preferred prodrug converting enzymes include nitroreductases, particularly those suitable for activating CB1954, and cytochrome P450 enzymes, particularly those most suitable for activating acetaminophen to NABQI. Preferred prodrugs accordingly include CB1954 and acetaminophen. However, in the case of cytochrome P450 enzymes, conventional cytotoxic prodrugs such as cyclophosphamide are also suitable.

In a further aspect of the invention, an isolated polynucleotide, or vector comprising such a polynucleotide or host cell comprising either, may encode, or express, a protein or peptide that is directly toxic to cells. In this case, no prodrug administration is required. Because of the self-contained nature of the joint/periprosthetic space surrounded by the interface tissue, it is possible to introduce vectors into this pathological space so that cells therein are transfected or transduced, causing them to express toxic products. Among the toxins that could be encoded and used in this way are ricin, abrin, diphtheria toxin, *Pseudomonas* exotoxin, DNase, RNase and botulinum toxin.

Preferably, the expression of such directly toxic molecules is under the control of a promoter providing substantially cell-type specific expression as herein described. In this way, expression of the toxin is restricted to target cells defined both by the physical constraints of the space into which the vector is introduced and the phenotype of the cells transfected or transduced. In this way, fibroblasts, or inflammatory cells such as activated cells of the monocyte/macrophage lineage, or specific cells such as osteoclasts and their precursors directly responsible for bone resorption, are targeted.

Accordingly, an isolated polynucleotide encoding a toxic peptide or protein is provided, wherein expression of the toxin is controlled by a promoter providing substantially cell-type specific expression. Preferably, this expression is restricted to cells of the monocyte/macrophage lineage. Alternatively, expression is restricted to fibroblasts. More preferably, expression is restricted to osteoclasts and osteoclast precursor cells. As described herein, suitable and preferred promoters include the c-fes and CD68 promoters to provide macrophage-specific expression and the TRAP, RANK and cathepsin K promoters to provide osteoclast-specific expression. Suitable and preferred toxins encoded include ricin, abrin, diphtheria toxin, *Pseudomonas* exotoxin, DNase, RNase and botulinum toxin.

Also provided is a vector comprising said polynucleotide and a host cell comprising either, and a pharmaceutical composition comprising an isolated polynucleotide or a vector as herein described, and a pharmaceutically acceptable excipient, carrier, diluent or buffer.

In a further embodiment is provided a product comprising an isolated polynucleotide, vector or host cell encoding or expressing a toxic peptide or protein as herein described, as a medication for the treatment of aseptic loosening of orthopaedic implants. Said expression may be under the control of a non-cell type specific promoter giving high levels of expression in cells of a variety of types. Preferably, said expression is controlled by a promoter providing substantially cell-type specific expression as herein described.

Also provided is the use of such products in the manufacture of a medicament for the treatment of aseptic loosening of orthopaedic implants.

In a further aspect is provided a kit for treatment of aseptic loosening of orthopaedic implants comprising:

a) An isolated polynucleotide or vector encoding an enzyme capable of converting a prodrug into an active cytotoxic compound, expression of which enzyme being controlled by an operably-linked promoter, in a pharmaceutically acceptable buffer;

b) A prodrug capable of being converted into an active cytotoxic compound by said enzyme, in a pharmaceutically acceptable buffer;

c) An tissue-digesting solution comprising at least one enzyme selected from the list consisting of collagenase, elastase, hyaluronidase, in a pharmaceutically acceptable buffer; and/or a chelator such as EDTA, EGTA etc.

d) A cement suitable for the refixation of said orthopaedic implant.

BRIEF DESCRIPTION OF THE FIGURES

FIG. 2 shows the killing effect of infection with nitroreductase-encoding adenoviral vectors and subsequent exposure to the prodrug CB1954 at the concentrations shown on interface cells from tissue taken from two revision surgery patients as described in Example 3.

Figure 4:
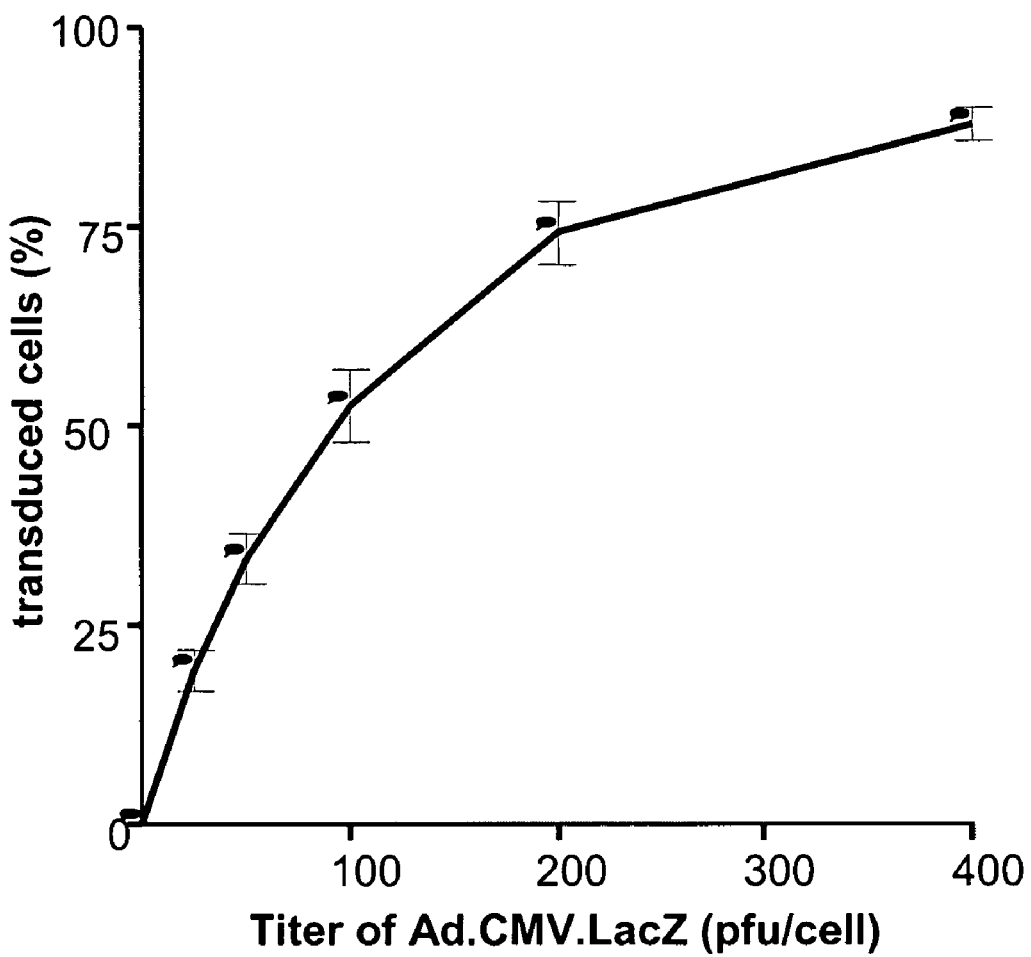

The numbered wells contain tissue treated as follows:

1. Noninfected interface tissue
2. Interface tissue+$3.6 \times 10^4$ pfu Ad.CMV.LacZ
3. Interface tissue+$3.6 \times 10^5$ pfu Ad.CMV.LacZ
4. Interface tissue+$3.6 \times 10^6$ pfu Ad.CMV.LacZ
5. Interface tissue+$3.6 \times 10^7$ pfu Ad.CMV.LacZ
6. Interface tissue+$3.6 \times 10^8$ pfu Ad.CMV.LacZ
7. Interface tissue+$3.6 \times 10^9$ pfu Ad.CMV.LacZ FIG. 4 shows transduction of interface cells following incubation with six different concentrations of Ad.CMV.LacZ (0, 25, 50, 100, 200 and 400 pfu/cell). After three days, cells were fixed and stained with X-gal reaction mix. The percentage of transduced (blue) cells was counted. The figure shows the means and standard deviations of 12 independent experiments.

Figure 5:
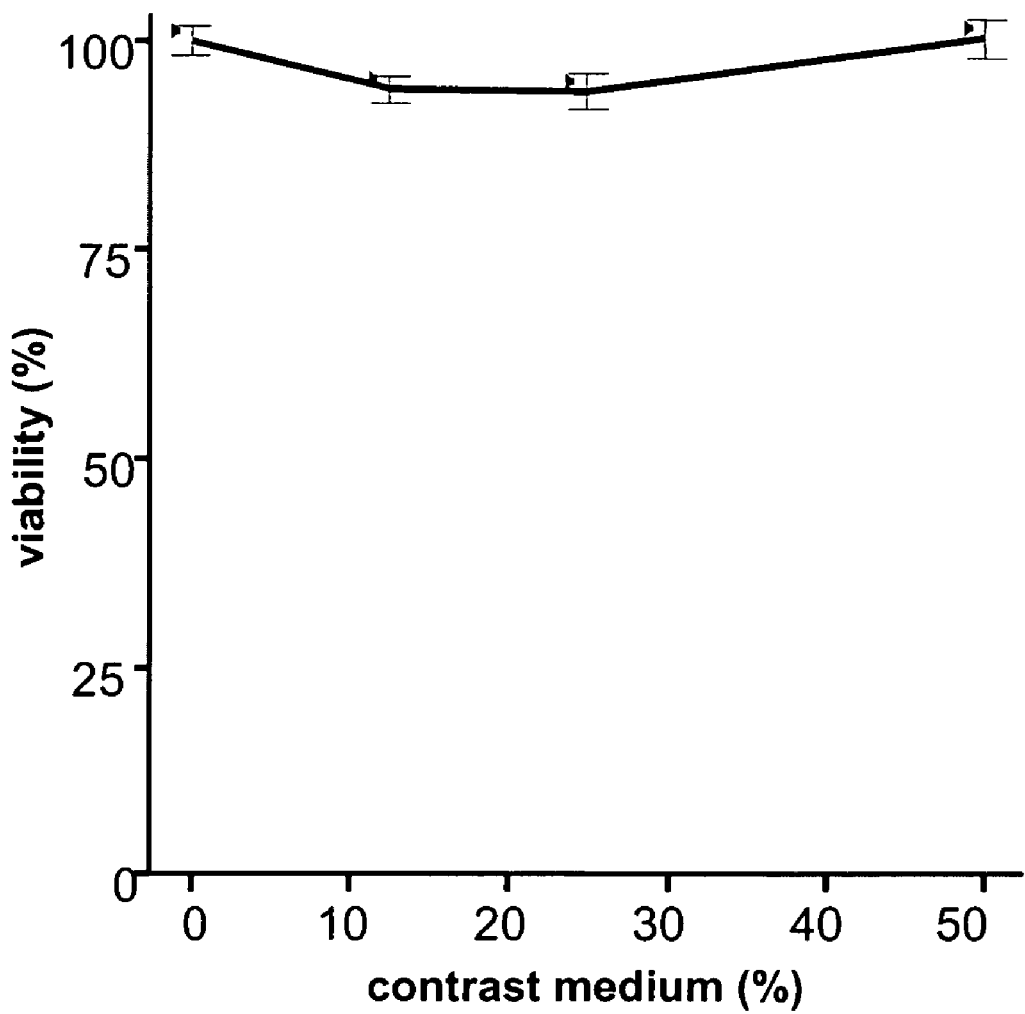

FIG. 5 shows the lack of toxicity of iotrolan (Isovist) contrast medium on interface cells. Interface cells were exposed to contrast medium (iotrolan) for 4 hours. After 3 days of cell culturing viability of the cells was measured (n=12).

Figure 6:
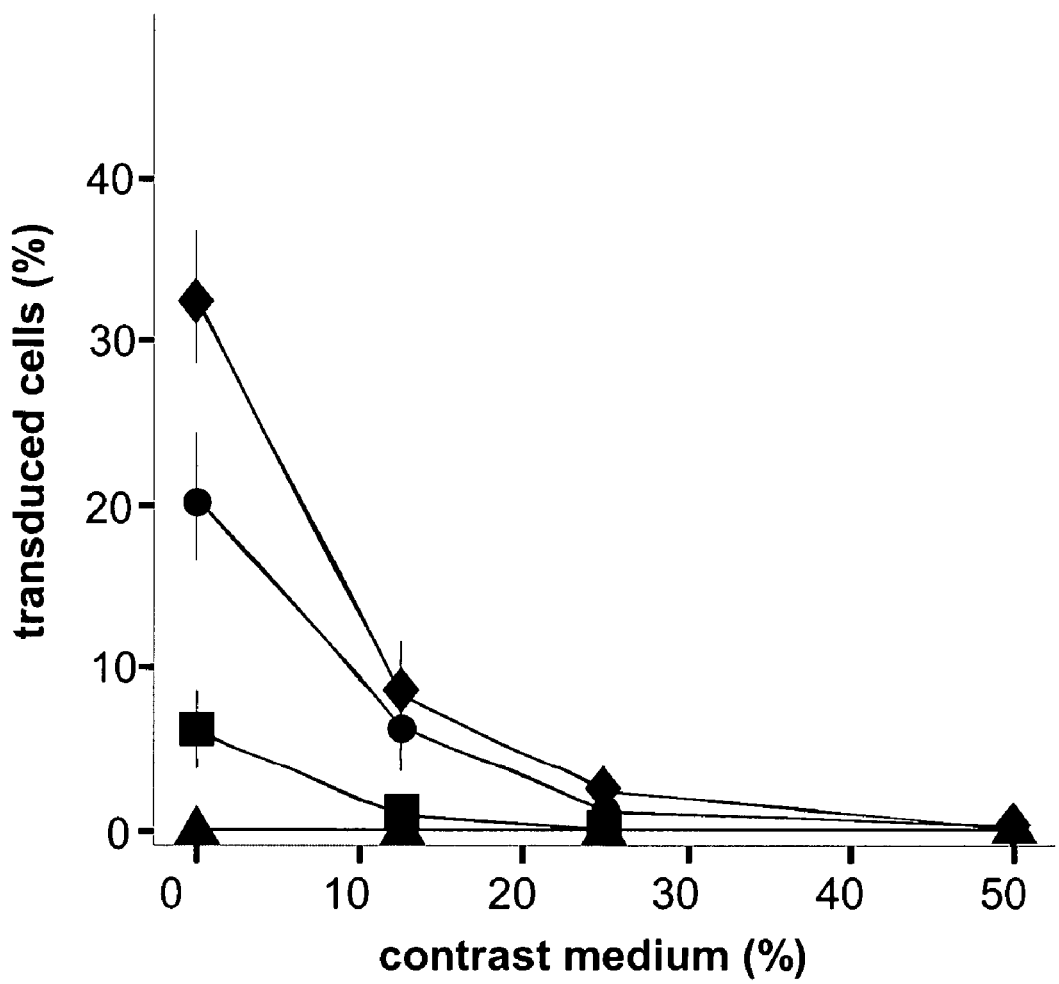

FIG. 6 shows the effect of iotrolan on HAdV5-transduction of interface cells. Cells were exposed to different concentrations of Ad.CMV.LacZ: ((▲) 0 pfu/cell, (■) 25 pfu/cell; (●) 100 pfu/cell; (♦) 200 pfu/cell. (n=4)) and contrast medium for four hours, after which the cells were fixed and stained with X-gal. Percentage of transduced cells was determined by counting blue cells.

Figure 7:
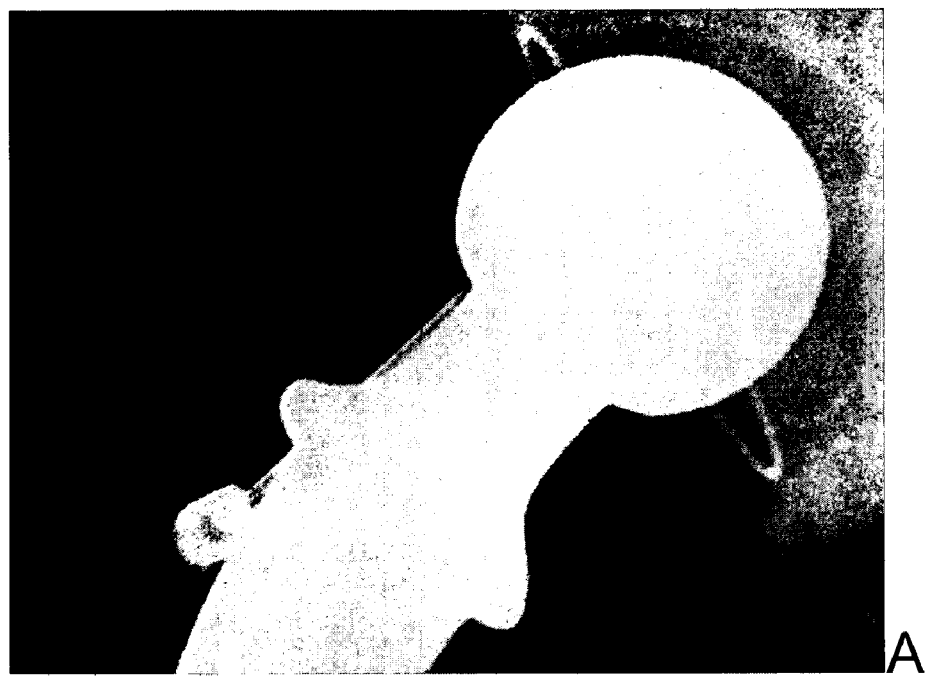
Figure 7:
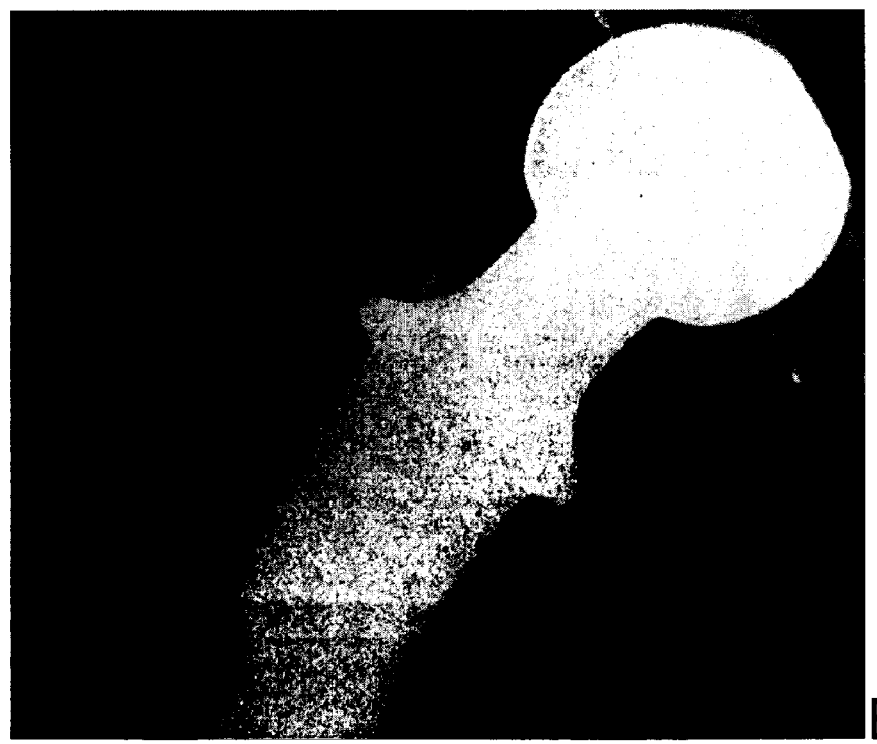

FIG. 7 shows pre- (A) and post-injection (B) images from Patient 1 showing an increased cement mass in the greater trochanteric region.

Figure 8:
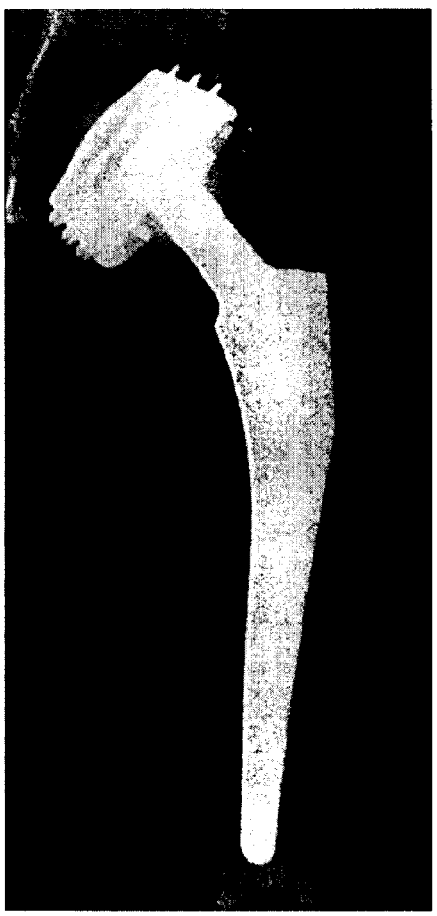
Figure 8:
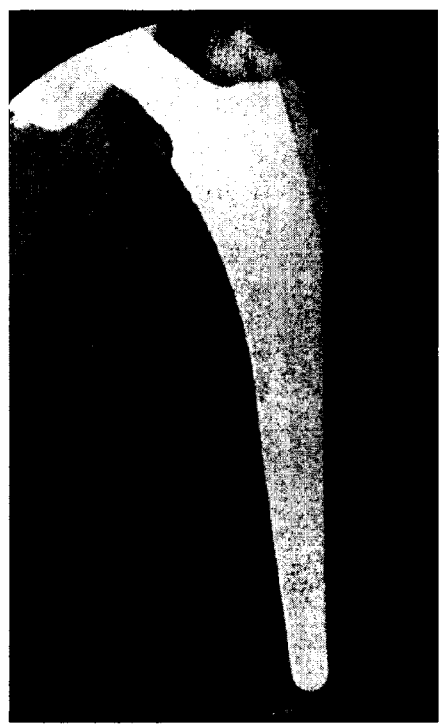

FIG. 8 shows pre- (A) and post-injection (B) images from Patient 2.

DETAILED DESCRIPTION OF THE INVENTION

The following examples are meant to illustrate the invention and do not limit it in any way. Persons of ordinary skill in the art will recognize modifications within the spirit and scope of the invention as set forth in the appended claims.

Example 1

Procedure for Treatment with CTL102(Ad5-NTR and CB1954)

Materials

The drug product, CTL102 injection, is a sterile, clear or virtually clear, aqueous liquid solution containing CTL102 virions at a nominal mean potency of $2\times10^{11}$ particles $ml^{-1}$, buffered at pH 7.4.

CB1954 is formulated as a sterile solution in solvent (N-methylpyrrolidone: polyethylene glycol, 2:7 v/v with 17.8 mg CB1954 $ml^{-1}$). Just prior to use, the prodrug in solvent is diluted in sterile saline to a maximum final CB1954 concentration of 5 mg $ml^{-1}$.

To stabilise the prosthesis, low viscosity bone cement (Simplex® P with tobramycin from Howmedica Inc, Rutherford, N.J., USA) is used. This radiopaque bone cement is a mixture of a liquid monomer component (2 ml 97.4% methylmethacrylate, 2.6% N,N-dimethyl-p-toluidine, 75 ppm hydroquinone) and a polymer powder (6 g polymethylmethacrylate, 30 g methylmethacrylate-styrene copolymer, 4 g barium sulphate, 1 g tobramycin sulphate). The components are vacuum mixed (0.9 bar, 1 minute) immediately before use.

For arthrography, Hexabrix 320 (ioxaglate sodium meglumine, Guerbet, Roissy Charles de Gaulle Cedex, France) contrast medium is used.

Procedure

Following careful flushing of the joint to remove synovial fluid and inflammatory exudate that may contain neutralizing anti-adenovirus antibodies, $3\times10^9$ pfu CTL102 is injected intra-articularly resulting in delivery of vector to cells throughout the periprosthetic space. After 48 hours, to allow transduction of target cells and expression of the nitroreductase transgene, CB1954 (at a dosage of 24 mg $m^{-2}$) is injected intra-articularly. To assure free access of CTL 102 and CB 1954 to the periprosthetic space it is preferred that patients are selected who have an arthrogram that shows contrast medium around the prosthesis. It is likely, therefore, that patients will usually undergo three arthrographies (one to assure access of contrast medium, one to inject the viral vector, and one to inject the CB 1954 prodrug).

In some circumstances after a number of days dead interface tissue may be removed by flushing or physical debridement, as appropriate. When the interface tissue is successfully diminished the prosthesis is refixated. To re-anchor the prosthesis to the bone, cement is injected in the periprosthetic space. For the flushing of the periprosthetic space and injection of the cement a number of holes are drilled through the bone into the periprosthetic space. This depends on the design of the prosthesis used. In many common designs, four is the minimum, because three holes are necessary for the femoral component to fixate in 3D space and one is necessary to fixate the acetabulum. As the bone biopsies are rather painful and the bone cannot be anaesthetised locally, these procedures are performed under general or spinal anaesthesia.

Example 2

Production of CTL102 (Ad5-NTR)

Materials and Methods

CTL102 was constructed as described in Djeha et al (2001) by homologous recombination in PerC6 helper cells. The cells were transfected at 90% confluence with an equimolar mixture of the transfer vector pTX0375 and the backbone vector pPS1160 complexed with Lipofectamine transfection reagent (Life Technologies).

pTX0375 was constructed in two stages: (i) the CMV promoter/enhancer fused to the NTR gene was excised from pTX0340 as a 1.5-kb BamHI-partial BgIII fragment and cloned into the unique BamHI site of pSW107, which is a pBluescript-based vector (Stratagene) that contains the human b-globin IVS II fused to the human complement 2 gene polyadenylation sequence adjacent to the BamHI site. A plasmid, pTX0374, which contains the CMV.NTR fragment in the required orientation, was identified by PCR using the T3 primer (5'-ATTAACCCTCAC-TAAAG-3') (SEQ ID NO:1) which anneals to the CMV promoter/enhancer, and an NTR primer, ECN2 (5'TCTGCTCGGCCTGTTCC-3') (SEQ ID NO:2). (ii) The complete NTR expression cassette was excised from pTX0374 as a 2.5-kb SpeI fragment and cloned into the unique SpeI site of the E1-deleted adenovirus transfer vector pPS1128 in the left-to-right orientation with respect to Ad5 sequences. pPS1128 is a pUC19-based plasmid that contains Ad5 sequences from the left-hand ITR to nucleotides (nt.) 359 fused to NT 3525-10589.

pPS1160 was constructed by PacI linearisation of pPS1128, ligation with a PacI-compatible adaptor (5'-TACATCTA-GATAAT-3' (SEQ ID NO: 3)+5'-P-TTATCTAGAT-GTA-3') (SEQ ID NO: 4) containing an XbaI site, followed by XbaI digestion to release a 7-kb XbaI fragment containing Ad5 sequences 3524-10589. This was then cloned into XbaI-linearised pPS1022, a pUC19-based plasmid containing Ad5 sequences from nt. 10589 to the right-hand ITR but lacking NT 28592 to 30470 (E3 region). Recombinants containing the fragment in the required orientation were identified by PCR using primers flanking the XbaI site at 10589 (rightward, 5'-TCGAGTCAAATACGTAGTCGT-3' (SEQ ID NO: 5); leftward, 5'-TGTTTCCGGAGGAATTTGCAA-3') (SEQ ID NO: 6). A plasmid, pPS1160/18, was confirmed to contain a single copy of the XbaI fragment (pPS1160/18) by HindIII and PstI digestion.

Transfected PerC6 cells were harvested following the appearance of extensive CPE (about 7-9 days after transfection) and recombinant virus released by three freeze-thaw cycles in infection medium (DMEM, 1% FCS, 2 mM $MgCl_2$). After two rounds of plaque purification on PerC6 cells the viruses were grown to large scale and purified by CsCl density centrifugation. Banded virus was dialysed against an excess of storage buffer (10 mM Tris, pH 7.4, 140 mM NaCl, 5 mM KCl, 0.6 mM $Na_2HPO_4$, 0.9 mM $CaCl_2$, 0.5 mM $MgCl_2$, and 5% sucrose), snap-frozen in aliquots in liquid nitrogen, and stored at $-280°$ C. Particle concentrations were determined using the BCA Protein Assay Reagent (Pierce, Rockford, Ill.) and the conversion factor 1 mg/ml=$3.4\times10^{12}$ virus particles/ml. Infectious titres were determined by plaque assay. Genomic DNA was isolated from banded adenovirus by digestion with proteinase K/SDS, phenol-chloroform extraction, and ethanol precipitation and characterised by restriction digestion.

Example 3

Killing of Interface Tissue from Patients with CTL102 and CB1954

In order to demonstrate the feasibility of using a virally delivered enzyme-prodrug system to kill interface cells, cells taken from two patients during revision surgery were cultured in vitro, incubated with CTL102 at a range of MOIs and subsequently exposed to CB1954. Cell viability was then determined using a metabolic activity assay.

Method

Interface Tissue Samples

For all experiments described, interface cells were used. Interface tissue was removed from the periprosthetic space during revision-surgery by an orthopedic surgeon and collected in sterile phosphate buffered saline (PBS). Connective tissue and fat were removed thoroughly and the interface tissue was digested for at least two hours at 37° C. using collagenase 1A (1 mg/ml; Sigma, St Louis, Mo., USA). Cells were then harvested by filtering the tissue/collagenase substance through a 200 μm filter (NPBI, Emmer-Compascuum, The Netherlands). The cells were cultured in 75 cm$^2$ flasks (Cellstar, Greiner, Alphen aan de Rijn, The Netherlands) with Iscove's modified Dulbecco's medium (IMDM; Biowitthaker, Verviers, Belgium), supplemented with glutamax (GibcoBRL, Paisley, UK), penicillin and streptomycin (Boehringer Mannheim, Germany), and 10% fetal calf serum (FCS; GibcoBRL, Paisley, UK) at 37° C. and 5% $CO_2$.

Before each experiment interface cells were detached from the flasks using 0.25% trypsin (GibcoBRL, Paisley, UK). The cells were counted in a bürker counter and death cells were excluded by trypan blue. Cells were seeded in a 96 wells-plate (flat bottom) at a density of 5,000 cells per well. Cells were incubated overnight to allow attachment to the bottom. Before each experiment the wells were washed twice with IMDM. For the experiments passage 2 to 4 interface cells were used. Light microscopy indicated that more than 95% of the cells were interface cells.

Transduction and Cell Killing Assay Protocol

Day 0: Interface cells from 2 patients were seeded at 5000 cells/well in IMDM (10% FCS) in 96 wells plates, 100 μl per well.

Day 1: Cells were infected with CTL102 (or diluent) at 0, 1, 5, 25, 100, 200 IU/cell in IMDM (10% FCS), 50 μl per well.

Day 2: Cells were washed twice with in IMDM (10% FCS), hereafter cells were incubated for 2 hr or 24 hr with CB1954 (or vehicle) at 0, 0.1, 0.5, 1, 5 and 50 μM in IMDM (10% FCS, 10% HS), 50 μl per well.

Day 2/3: Cells were washed once with IMDM (10% FCS) and then incubated in IMDM (10% FCS, 10% HS), 5 μl per well.

Day 4: Photographs were taken. Medium was refreshed with IMDM (10% FCS), 10 μl WST reagent (Roche) was added and the plates were incubated for 2 hr.

Hereafter the absorbance at 415 nm was measured.

Results

Figure 1:
FIG. 1 depicts aseptic loosening of a hip prosthesis. A is a radiograph of loosened prosthesis in situ. B is an arthrogram of a hip joint with a loosened prosthesis. The contrast medium is injected into the joint space under fluoroscopic guidance. The picture shows that a part of the area around the prosthesis (periprosthetic space) is filled with contrast medium. This proves that the prosthesis is loose in that area. C shows a schematic representation of a hip joint with a loosened prosthesis. The gray area indicates the joint space, which is continuous with the periprosthetic space. When injecting a fluid into the joint space, this will spread through the area which is marked gray in the image.
Figure 1:
Figure 1:
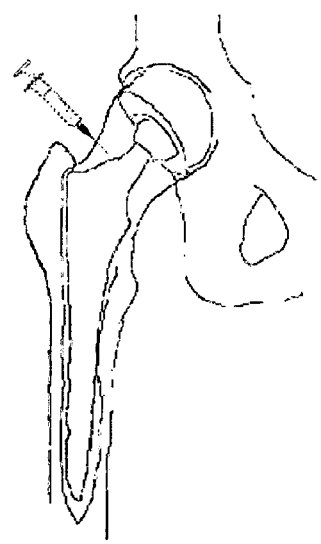
Figure 2A:
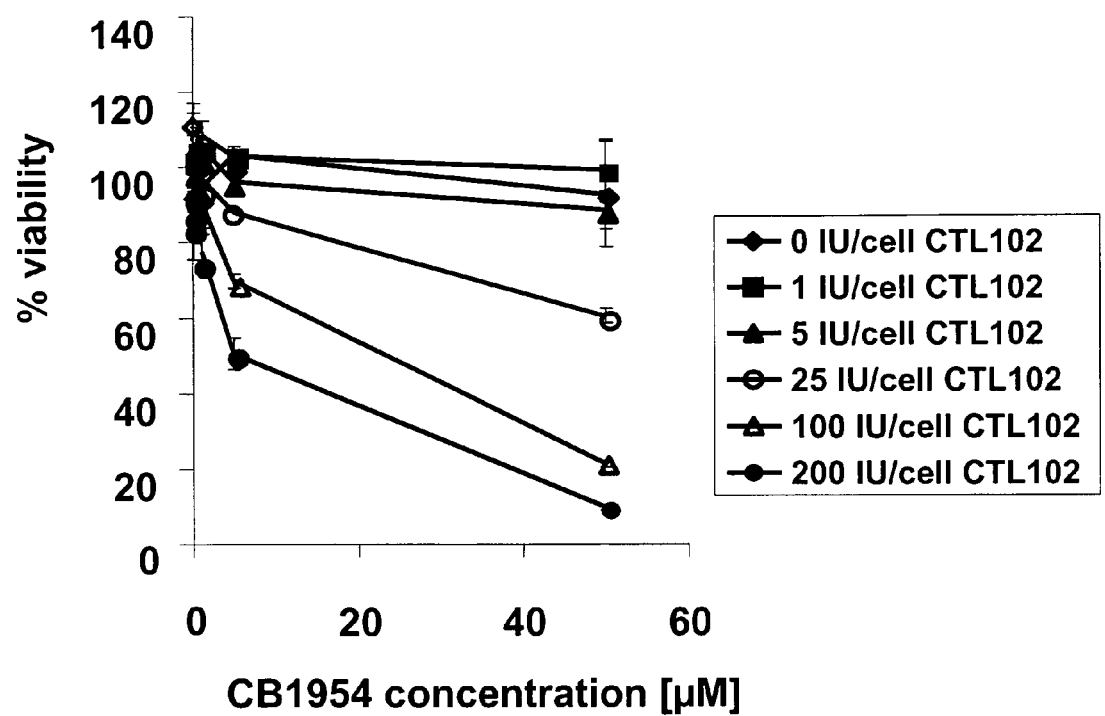
FIG. 2a shows data from patient LI003 P3 and FIG. 2b shows data from patient LI002 P4.
Figure 2B:
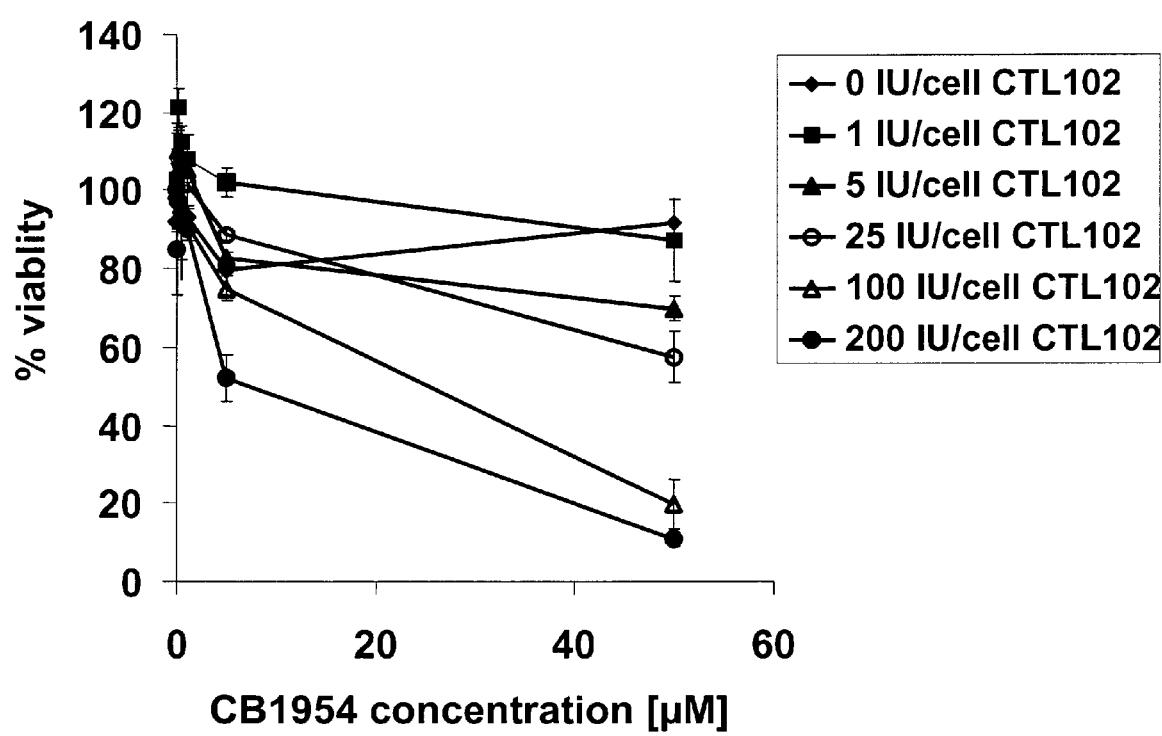

As shown in FIGS. 2A and 2B, virus and CB1954-dose dependent killing was observed for cells from both patients. Importantly, efficient (90%) killing was observed with virus and CB1954 doses (200 virus pfu/cell and a CB1954 concentration of 50 μM) that is readily achievable in the clinic.

These results demonstrate that interface cells can be transduced by an HAdV-5-vector and killed by the NTR/CB1954 approach. Human adenovirus 5 is capable of infecting a broad range of dividing and non-dividing human cells including fibroblasts and macrophages (Djeha et al, 2001).

Killing of cells by GDEPT has been studied before in various cell lines, using various approaches. The NTR/CB1954 approach is attractive for clinical evaluation for several reasons: (1) it generates a toxic agent that can kill both dividing and non-dividing cells, (2) induction of cell death occurs by a p53-independent mechanism, and (3) CB1954 is well-tolerated in man (Djeha et al, 2001). Cell killing by the NTR/CB1954 approach has been proved effective in a variety of human cancer cells (Chung-Faye et al, 2001; Bilsland et al, 2003, Green et al, 2003; McNeish et al, 1998; Shibata et al, 2002; Weedon et al, 2000; Wilson et al, 2002), but has not previously been studied in synovial or interface cells. The current study shows that interface cells can be effectively killed by the NTR/CB1954 approach.

For the current study passage 2 to 4 interface cells were used. These passages were used to maximally reduce culture artefacts. On the one hand, in very low passages (0 and 1) there is a risk for presence of contaminating cells (especially macrophages), which decreases with higher passages. On the other hand, at higher passages the risk of substantial in vitro alteration/growth selection exists (especially at passages higher than 4) (Zimmerman et al, 2001). In the current study, cultured interface cells of different patients were used. For the interpretation of the results the data of all patients were pooled. However, it must be noted that individual differences in transducibility were observed.

Example 4

Efficient Infection of Intact Interface Tissue with Adenovirus Vectors

Figure 3:
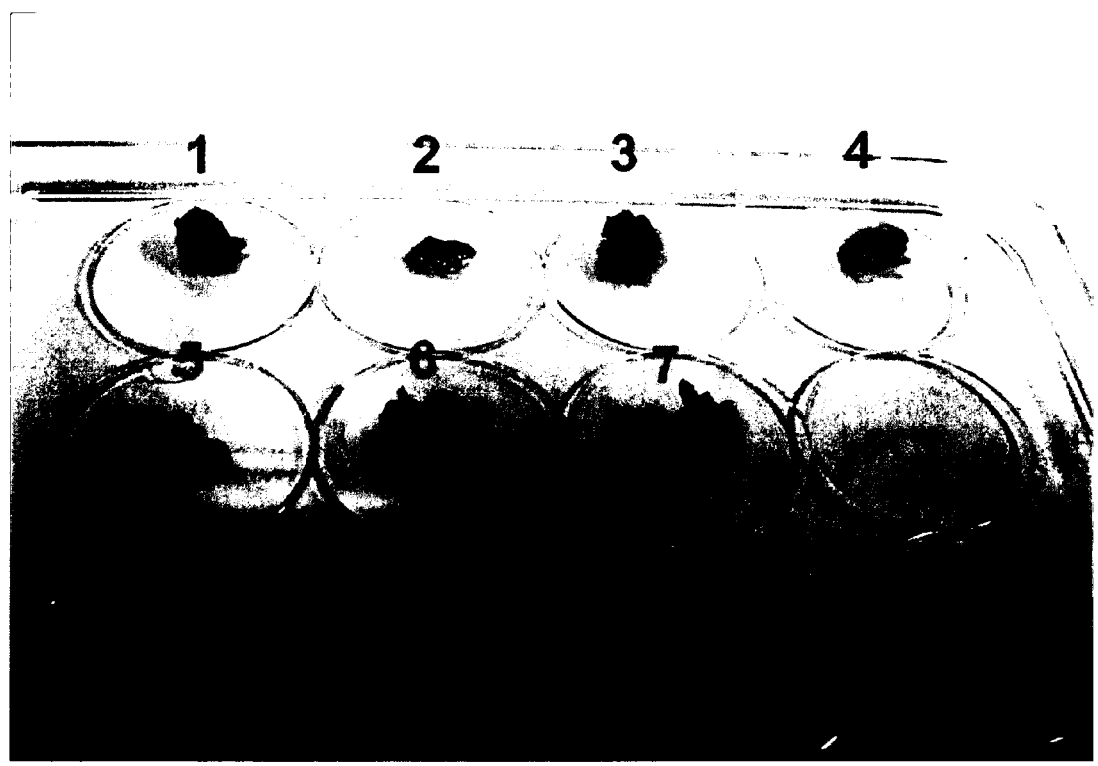
FIG. 3 shows the results of X-Gal staining of samples of intact interface tissue taken from patient LI014 infected with various doses of a Lac Z-encoding adenoviral vector, as described in Example 4.

The experiment outlined in Example 3 confirmed that cultured interface cells are Ad5-infectable. However, when a cell is present within an intact tissue, access of the virus to the cell surface may be prevented, for instance by the extracellular matrix and by the low rate of virus diffusion through the extracellular space. In view of this, the infectability of fresh intact interface tissue was examined using a LacZ-expressing adenovirus and XgaI staining of LacZ-expressing tissue. Using this approach, a virus dose-dependent increase in gene expression was observed, with strong levels of gene expression with the two highest virus doses tested (FIG. 3).

Method

Interface tissue (LI014) was obtained from a revision operation of the hip of a rheumatoid arthritis patient. The tissue was cut in 7 pieces and the pieces were put in 10 ml round bottom tubes. Different concentrations of Ad.CMV.LacZ (0, $3.6 \times 10^4$, $3.6 \times 10^5$, $3.6 \times 10^6$, $3.6 \times 10^7$, $3.6 \times 10^8$, $3.6 \times 10^9$ pfu) in 200 μl IMDM/10% FCS were added. The tissues were incubated at 37° C. for 2 hours, the tubes were shaken every 10 to 15 minutes. Hereafter 5 ml IMDM/10% FCS was added and after an overnight incubation the tissues were rinsed 3× with PBS and subsequently put in 5 ml XgaI colouring solution and incubated for 3.5 hours at 37° C. The tissues were rinsed 3× with PBS and fixed in 10% formalin.

Results

The tissues with the highest added amounts of Ad.CMV.LacZ have areas of dark blue staining, which is evident down to an infection at $3.6 \times 10^7$ pfu Ad.CMV.LacZ. Demonstrating that infection of cells in intact interface tissue is effective.

Embedded paraffin sections of the tissues were examined microscopically and the presence of stained, infected cells was confirmed.

Example 5

Transduction of Interface Tissue and Effect of Contrast Medium

To test further the susceptibility of interface cells to human adenovirus 5 (HAdV-5)-based vectors, primary cultures of interface cells were exposed to the HAdV-5 vector Ad.CMV.LacZ. Twenty-four hours post-infection the cells were stained with X-gal solution for β-galactosidase reporter gene expression. The transduction efficiency increased with increasing vector concentration. At 400 plaque forming units/cell the percentage of cells expressing the reporter gene was 88% (sd 4.0) (FIG. 4). Thus HAdV-5 vectors can transduce interface cells.

Materials and Methods

Adenoviral Vectors

The Ad.CMV.LacZ (van der Eb et al, 2002) vector is identical to CTL102, but the *E. coli* lacZ gene replaces the ntr gene.

Transduction Assays

To study the transducibility of interface cells by HAdV-5, interface cells were infected with Ad.CMV.LacZ vector (in concentrations of 0, 25, 50, 100, 200, 400 pfu/cell).

Twenty-four hours post infection the cells were washed twice with IMDM, and cultured for two days. Medium was refreshed each day. On day three, the monolayer cultures were washed twice with PBS and fixed with 0.2% glutaraldehyde and 2% formaldehyde in PBS for 10 minutes at 4° C. Subsequently cells were washed twice with PBS and stained for β-galactosidase activity in 50 μl of reaction mix (1 mg/ml XgaI (Eurogentec, Seraing, Belgium), 5 mM potassium ferrocyanide, 5 mM potassium ferricyanide, 2 mM $MgCl_2$ in PBS) for 2 hours at 37° C. The percentage of transduced cells was assessed by counting at least 100 interface cells, using light microscopy. All conditions were tested in duplicate.

Effect of Contrast Medium on Interface Cells

Interface cells were seeded in 96-wells plates. Into each well 50 μl of IMDM/20% FCS and 50 μl of a solution containing contrast medium and 0.9% NaCl in various concentrations (0, 12.5, 25, and 50% contrast medium) were added. The contrast medium used was the low-osmolarity, nonionic dimer iotrolan (Isovist; Schering, Berlin, Germany). After four hours of exposure to the contrast medium, the cells were washed twice and incubated in IMDM/10% FCS. The cells were cultured for three more days, changing the culture medium every day. On day four, cell viability was determined with the WST-1 cell viability assay kit (Roche, Mannheim, Germany) according to the manufacturers protocol.

Effect of Contrast Medium on HAdV-5-Transduction of Interface Cells

Interface cells were seeded in 96-wells plates. After overnight incubation cells were infected with Ad.CMV.LacZ (concentrations of 0, 25, 100, and 200 pfu/cell) in IMDM/20% FCS, 50 μl per well. Fifty μl Iotrolan (Isovist) in 0.9% NaCl was added in concentrations of 0, 25, 50, and 100%. (When diluted in the culture medium these concentrations decreased to 0, 12.5, 25, and 50%.) Four hours after infection, the cells were washed twice with IMDM and incubated for the rest of the day in IMDM/10% FCS at 37° C. and 5% $CO_2$. The Ad.CMV.LacZ transduced cells were cultured for three days after removal of the vector and contrast medium. Subsequently, the cells were fixed and stained for β-galactasidase activity. The transduction rate was assessed as described above.

Statistical Analysis

A univariate analysis of variance and Spearman's correlation was used to study the interaction between vector and prodrug and between vector and contrast medium and to study the effect of CB1954 on viability of the cells. A Mann-Whitney test for independent groups was performed to determine the difference in cell killing between the cells that were exposed to contrast medium and the non-exposed cells. In the experiment to study the effect of transient exposure to contrast medium on transduction of HAdV-5-vector Spearman's correlation between contact time and viability and between delay time and viability was tested. For all statistical analyses p<0.05 was the level of statistical significance.

Results

Effect of Contrast Medium on Interface Cells

The toxicity of contrast medium (iotrolan) on interface cells was evaluated (FIG. 5). Iotrolan does not affect the viability of the cells at any concentration (p=0.563).

Adding of contrast medium to the interface cells for four hours does not lead to killing of the cells.

Effect of Contrast Medium on HAdV-5 Transduction of Interface Cells

The effect of contrast medium (iotrolan) on HAdV5-transduction of interface cells was investigated with Ad.CMV.LacZ. Transducibility of the cells increases with the concentration of HAdV-5 vector. However, the contrast medium has restraining influence on the transduction efficiency. With higher concentrations of iotrolan, the HAdV-5 vector concentration has less effect on gene transfer efficiency. At a contrast medium concentration of 50% none of the cells were transduced (FIG. 6). The effect of iotrolan on the transduction is statistically significant (p<0.001). Furthermore, differences between cells from different individuals (n=6) have been observed. To evaluate the effect of contrast medium on cell killing by NTR/CB1954, the previously described experiment for the efficiency of cell killing was repeated in the presence of contrast medium. The results showed that, in the presence of contrast medium, cells are not killed by the NTR/CB1954 approach (results not shown). The presence of Hexabrix 320 contrast medium also inhibited viral transduction (data not shown). In summary, the results from these experiments demonstrate the incompatibility of viral administration in combination with the administration of two commonly used contrast media. This incompatibility may be due to the presence of iodine within the contrast media. Screening of all available contrast media may allow determination of a contrast medium compatible with viral transduction.

The influence of transient exposure to contrast medium on the transduction of interface cells was investigated. Interface cells were exposed to contrast medium for 0 to 120 minutes and the period between washing away of the contrast medium and performing the NTR/CB1954 cell killing approach was varied. Cell killing was not correlated with contact time (corr −0.033, p=0.691) or length of period between washing away of the contrast medium and addition of the vector (corr −0.004, p=0.962). Killing of cells not exposed to contrast medium and those transiently exposed was equivalent.

Discussion

In this study the influence of contrast medium on cell killing by NTR/CB1954 was investigated in view of future clinical studies. Results show that the contrast medium does not seem to have any influence on the interface cells. However, transduction of the cells by an adenoviral vector, in the presence of contrast medium, is almost negligible. The adenoviral vector is inactivated by the presence of contrast medium. In a putative clinical study the viral vector will be injected in the joint space. Normally, contrast medium is used to verify the position of the needle in the joint. The results of this study however show that the use of contrast medium in combination with a viral vector is dissuaded. Thus, for a clinical study, we propose that alternative methods for the visualization of the needle should be employed such as injection of air to create an "air-arthrogram".

In conclusion, this example shows that interface cells can be killed by the NTR/CB1954 enzyme prodrug approach.

Example 6

Clinical Outcomes

Data are available from the first two patients from a phase-1 study of 12 patients with a loosened hip experiencing debilitating pain and significant comorbidity. On day 1 the vector was injected into the hip joint and the prodrug injected on day 3, as described above. On day 10 three holes were drilled in the femur and one in the acetabulum. Biopsies are taken from the periprosthetic space and low viscosity cement (Osteopal, Biomet Merck, Sjöbo, Sweden) injected under fluoroscopic guidance.

Patient 1 is an 82-year old female with loosening of both hip prostheses, classified ASA IV (mortality risk 20.3%, American Society of Anesthesiologists physical status classification, Saklad, 1941). There were no adverse effects from vector injection ($3\times10^9$ particles) and 24 hours post-injection there was no detectable virus shedding. Twelve hours after prodrug injection the patient experienced nausea, (WHO grade 1) which was known as a reaction to the prodrug. Also hip pain increased, which was anticipated as the initial therapy is intended to cause more loosening. 16 ml of cement was injected into periprosthetic space (see FIG. 7B) indicating significant destruction of interface tissue creating a void into which cement could now be introduced. The patient was ambulated the day after surgery.

At two and four weeks after cement injection the patient had no pain in the treated hip, and was still improving. The maximum walking distance had increased from 4-5 metres to 30 metres. Subjective walking distance assessed by the patient (0: 0 metres, 100: unlimited walking distance) increased from 4 to 66. The patient's pain score (0: no pain, 100: unbearable pain) decreased from 81 preoperatively to 2. In addition, she could now sleep on her side without pain, which she had been unable to do for four years. In terms of perceived dependency (0: completely dependent on others, 100: completely independent) the score decreased from 95 to 54.

Patient 2 is a 72 year old woman with loosening of her left hip prosthesis and an ASA classification of II (mortality risk 2.8%). Again, there was no detectable virus shedding 24 hours after vector injection. 18 ml of cement was injected following a similar procedure (FIG. 8B). Four weeks post-treatment the pain score had decreased from 43 to 22 (probably reflecting the presence of a post-operative haematoma, requiring 4-5 weeks to resolve). Specifically hip joint-related pain disappeared. Maximum walking distance increased from 500 to 2000 metres. By the 3 month follow-up, the haematoma had completely resolved and pain score had further decreased to 7. The patient continues to improve in terms of walking performance and other activities.

The current study is the first to use in vivo intra-articular adenoviral mediated gene transfer in a clinical setting. The preliminary results suggest that gene therapy and cement injection for hip prosthesis refixation is clinically feasible.

All references cited herein are hereby incorporated by reference in their entireties.

REFERENCES

1. Anderson W F (1998) Human gene therapy. Nature 392: (6679 Suppl): 25-30.
2. Bilsland, A. E., et al. (2003). Selective ablation of human cancer cells by telomerase-specific adenoviral suicide gene therapy vectors expressing bacterial nitroreductase. Oncogene 22: 370-380.
3. Calos M P (1996). The potential of extrachromosomal replicating vectors for gene therapy. Trends in Genetics 12: 463-466.
4. Chen L and Waxman D J (2002) Cytochrome P450 gene-directed enzyme prodrug therapy (GDEPT) for cancer. Curr Pharm Des 8: 1405-1416.
5. Chung-Faye, G., et al. (2001). Virus-directed, enzyme prodrug therapy with nitroimidazole reductase: a phase I and pharmacokinetic study of its prodrug, CB1954. Clin. Cancer Res. 7: 2662-2668.
6. Cotten M, Wagner E and Birnstiel M L (1992) Receptor-mediated transport of DNA into eukaryotic cells. Meth Enzymol 217: 618-644.
7. Djeha, Thomson, Leung, Searle, Young, Kerr, Harris, Mountain, and Wrighton (2001). Combined adenovirus-mediated nitroreductase gene delivery and CB1954 treatment: a well-tolerated therapy for established solid tumors. Mol Ther 3: 233-240.
8. Eggelmeijer, Papapoulos, Van Paassen, Dijkmans, Valkema, Westedt, Landman, Pauwels and Breedveld (1996). Arthritis Rheum 39: 396-402.
9. Emerson S G (1996). Ex vivo expansion of hematopoietic precursors, progenitors, and stem cells: the next generation of cellular therapeutics. Blood 87, 3082-3088.
10. Flotte T R, Afione S A, Conrad C, McGrath S A, Solow R, Oka H, Zeitlin P L, Guggino W B and Carter B J (1993). Stable in vivo expression of the cystic fibrosis transmembrane conductance regulator with an adeno-associated virus vector. Proc Natl Acad Sci USA 90: 10613-10617.
11. Friedlos, Quinn, Knox and Roberts (1992). The properties of total adducts and interstrand crosslinks in the DNA of cells treated with CB 1954. Exceptional frequency and stability of the crosslink. Biochem Pharmacol 43: 1249-1254.
12. Goldring, Jasty, Roelke, Rourke, Bringhurst and Harris (1986). Formation of a synovial-like membrane at the bone-cement interface. Its role in bone resorption and implant loosening after total hip replacements. Arthritis Rheum 29: 575-584.
13. Goosens P H, Schouten G J, 't Hart B A, Brok H P, Kluin P M, Breedveld F C, Valerio D and Huizinga T W (1999). Feasibility of adenovirus-mediated nonsurgical synovectomy in collagen-induced arthritis-affected rhesus monkeys. Hum Gene Ther 10: 1139-1149.
14. Greaves and Gordon (2002). Macrophage-specific gene expression: current paradigms and future challenges. Int J Hematol 76: 6-15.
15. Green, N. K., McNeish, I. A., Doshi, R., Searle, P. F., Kerr, D. J., Young, L. S. (2003). Immune enhancement of nitroreductase-induced cytotoxicity: studies using a bicistronic adenovirus vector. Int. J. Cancer 104: 104-112.
16. Grove, Searle, Weedon, Green, McNeish and Kerr (1999). Virus-directed enzyme prodrug therapy using CB1954. Anti-Cancer Drug Design 14: 461-472.
17. Hellman, Capello and Feinberg (1999). Omnifit cementless total hip arthroplasty: a 10 year average follow-up. Clin Orthop 364: 164-174.
18. Hengge U R, Chan E F, Foster R A, Walker P S and Vogel J C (1995) Cytokine gene expression in epidermis with biological effects following injection of naked DNA. Nature Genet 10: 161-166.
19. Hickman M A, Malone R W, Lehmann-Bruinsma K, Sih T R, Knoell D, Szoka F C, Walzem R, Carlson D M and 19. Powell J S (1994). Gene expression following direct injection of DNA into liver. Human Gene Therapy 5: 1477-1483.
20. Hitt, M M, Addison C L and Graham, F L (1997) Human adenovirus vectors for gene transfer into mammalian cells. Advances in Pharmacology 40: 137-206.
21. Keown W A, Campbell C R, Kucherlapati R S (1990). Methods for introducing DNA into mammalian cells. Methods Enzymol 185: 527-37.
22. Knox R J, Boland M P, Friedlos F et al (1988) Biochemical Pharmacology 37:4671-4677.
23. Knox, Friedlos, Marchbank and Roberts (1991). Bioactivation of CB 1954: reaction of the active 4-hydroxylamino derivative with thioesters to form the ultimate DNA-DNA interstrand crosslinking species. Biochem Pharmacol 42: 1691-1697.
24. Kucherlapati and Skoultchi (1984) Introduction of purified genes into mammalian cells. CRC Crit. Rev. Biochem 16: 349-379.
25. Leung, Scammell, Lyons, Czachur, Gilbert, Freedholm, Malbecq, Miller, Carr and Checkley (1999). Alendronate prevents periprosthetic bone loss—2 year results. Arthritis Rheum 42 (Suppl): S270.
26. Mack K D, Walzem R and Zeldis J B (1994). Cationic lipid enhances in vitro receptor-mediated transfection. Am J Med Sci 307: 138-143.
27. Mansky, Sulzbacher, Purdom, Nelsen, Hume, Rehli and Ostrowski (2002). The microphthalmia transcription factor and the related helix-loop-helix zipper factors TFE-3 and TFE-C collaborate to activate the tartrate-resistant acid phosphatase promoter. J Leukoc Biol 71: 304-310.
28. McNeish, Searle, Young and Kerr (1997). Gene-directed enzyme prodrug therapy for cancer. Advanced Drug Delivery Reviews 26: 173-184.
29. McNeish, I. A., et al. (1998). Virus directed enzyme prodrug therapy for ovarian and pancreatic cancer using retrovirally delivered E. coli nitroreductase and CB1954. Gene Ther. 5: 1061-1069.
30. Meyer K B, Thompson M M, Levy M Y, Barron L G and Szoka F C Jr. (1995). Intratracheal gene delivery to the mouse airway: characterization of plasmid DNA expression and pharmacokinetics. Gene Therapy, 2, 450-460, 1995
31. Miller J L, Donahue R E, Sellers S E, Samulski R J, Young N S and Nienhuis A W (1994). Recombinant adeno-associated virus (rAAV)-mediated expression of a human gamma-globin gene in human progenitor-derived erythroid cells. Proc Natl Acad Sci USA 91:10183-10187.
32. Moolten F L et al (1986) Tumour chemosensitivity conferred by inserted herpes thymidine kinase genes: Paradigm for a prospective cancer control strategy. Cancer Res 46:5276-5281.
33. Motyckova, Weilbaecher, Horstmann, Riemann, Fisher and Fisher (2001). Linking osteopetrosis and pycdysostosis: regulation of cathepsin K expression by the microphthalmia transcription factor family. Proc Natl Acad Sci USA 98: 5798-5803.
34. Mullen C A, Kilstrup M and Blaese R M (1992) Transfer of the bacterial gene for cytosine deaminase to mammalian cells confers lethal sensitivity to 5-fluorocytosine: A negative selection system. PNAS USA 89:33-37.
35. NHS Centre for Reviews & Dissemination (1996). Total hip replacement. Effective Health Care. Volume 2. Number 7. Churchill-Livingstone.
36. NIH Consensus Statement Online (1994). Total Hip Replacement. Sep. 12-14 1994, 12 (5): 1-31.
37. Nishikawa M and Huang L (2001). Nonviral vectors in the new millennium: Delivery barriers in gene transfer. Human Gene Therapy 12:861-870.
38. Philip R, Brunette E, Kilinski L, Murugesh D, McNally M A, Ucar K, Rosenblatt J, Okarma T B and Lebkowski J S (1994). Efficient and sustained gene expression in primary T lymphocytes and primary and cultured tumor cells mediated by adeno-associated virus plasmid DNA complexed to cationic liposomes. Mol Cell Biol 14: 2411-2418.
39. Plank C, Oberhauser B, Mechtler K, Koch C and Wagner E (1994). The influence of endosome-disruptive peptides on gene transfer using synthetic virus-like gene transfer systems. J Biol Chem 269: 12918-12924.
40. Ralston, Hacking, Willocks, Bruce and Pitkeathly (1989). Clinical, biochemical and radiographic effects of amino-hydroxypropylidene bisphosphonate treatment in rheumatoid arthritis. Ann Rheum Dis 48: 396-399.
41. Russell D W, Miller A D and Alexander I E (1994). Adeno-associated virus vectors preferentially transduce cells in S phase. Proc Natl Acad Sci USA 91: 8915-8919.
42. Saklad M (1941) Grading of patients for surgical procedures. Anesthesiology 2: 281-284.
43. Shanbhag, Hasselman and Rubash (1997). The John Charnley Award. Inhibition of wear debris mediated osteolysis in a canine total hip arthroplasty model. Clin Orthop 344: 33-43.
44. Shibata, T., Giaccia, A. J., Brown, J. M. (2002). Hypoxia-inducible regulation of a prodrug-activating enzyme for tumor-specific gene therapy. Neoplasia 4: 40-48.
45. Sikes M L, O'Malley B W Jr, Finegold M J, Ledley F D (1994). In vivo gene transfer into rabbit thyroid follicular cells by direct DNA injection. Human Gene Therapy 5: 837-844.
46. Strehle J, DelNotaro C, Orler R and Isler B (2000) The outcome of revision hip arthroplasty in patients older than age 80 years. Complications and social outcome of different risk groups. J Arthroplasty 15:690-697.
47. Teitelbaum (2000). Bone resorption by osteoclasts. Science 289: 1504-1508.
48. Trubetskoy V S, Torchilin V P, Kennel S J, Huang L (1992). Use of N-terminal modified poly(L-lysine)-antibody conjugate as a carrier for targeted gene delivery in mouse lung endothelial cells. Bioconjugate Chem 3: 323-327
49. Ulrich-Vinther, Carmody, Goater, Søballe, O'Keefe, and Schwarz (2002). Recombinant adeno-associated virus-mediated osteoprotegerin gene therapy inhibits wear debris-induced osteolysis. J Bone Joint Surg 84A: 1405-1412.
50. Ustav M and Stenlund A (1991). Transient replication of BPV-1 requires two viral polypeptides encoded by the E1 and E2 open reading frames. EMBO J. 10: 449-457
51. van der Eb, M. M., et al. (2002). Gene therapy with apoptin induces regression of xenografted human hepatomas. Cancer Gene Ther. 9: 53-61.
52. Vile R G and Hart I R (1993). In vitro and in vivo targeting of gene expression to melanoma cells. Cancer Res 53: 962-967.
53. Walsh C E, Liu J M, Xiao X, Young N S, Nienhuis A W, Samulski R J (1994). Regulated high level expression of a human gamma-globin gene introduced into erythroid cells by an adeno-associated virus vector. Proc Natl Acad Sci USA 89: 7257-7261.
54. Weedon, S. J., et al. (2000). Sensitisation of human carcinoma cells to the prodrug CB1954 by adenovirus vector-mediated expression of E. coli nitroreductase. Int. J. Cancer 86: 848-854.

55. Wilson J M, Grossman M, Wu C H, Chowdhury N R, Wu G Y and Chowdhury J R (1992). Hepatocyte-directed gene transfer in vivo leads to transient improvement of hypercholesterolemia in low density lipoprotein receptor-deficient rabbits. J Biol Chem 267: 963-967.
56. Wilson, W. R., Pullen, S. M., Hogg, A., Helsby, N. A., Hicks, K. O., Denny, W. A. (2002). Quantitation of bystander effects in nitroreductase suicide gene therapy using three-dimensional cell cultures. Cancer Res. 62: 1425-1432.
57. Wolff J A, Malone R W, Williams P, Chong W, Acsadi G, Jani A and Felgner P L (1990). Direct gene transfer into mouse muscle in vivo. Science 247:1465-1468.
58. Wooley P H and Schwarz E M (2004). Aseptic loosening. Gene Therapy 11: 402-407.
59. Wu G Y and Wu C H (1988). Receptor-mediated gene delivery and expression in vivo. J Biol Chem 263:14621.
60. Weir N (1999) Non-viral vectors for gene therapy. In "Biotechnology—A multi-volume, comprehensive treatise", Volume 5a, Recombinant proteins, monoclonal antibodies and therapeutic genes, Ed by A. Mountain, U. Ney and D, Schomburg, Wiley VCH Verlag.
61. Zimmermann, T., et al. (2001). Isolation and characterization of rheumatoid arthritis synovial fibroblasts from primary culture—primary culture cells markedly differ from fourth-passage cells. Arthritis Res. 3: 72-76.

What is claimed is:

1. A method for reducing interface tissue causing aseptic loosening of orthopaedic implants comprising:
   (a) administering by intra-articular or periposthetic injection an effective amount of an adenoviral vector comprising an isolated polynucleotide encoding nitroreductase to interface tissue cells;
   (b) administering an effective amount of prodrug CB 1954 (5-(aziridin-1-yl)-2,4-dinitrobenzamide), to said interface tissue; and
   (c) allowing the expression of said nitroreductase in said interface tissue cells, wherein interface tissue is reduced.

2. A method of treating aseptic loosening of orthopaedic implants comprising
   (a) administering by intra-articular or periposthetic injection to a human or other animal an effective amount of an adenoviral vector comprising an isolated polynucleotide encoding nitroreductase to interface tissue cells;
   (b) allowing the expression of said nitroreductase in said interface tissue cells;
   (c) administering an effective amount of prodrug CB 1954 (5-(aziridin-1-yl)-2,4-dinitrobenzamide), to said interface tissue;
   (d) refixing the orthopaedic implant.

* * * * *

SEQUENCE LISTING

<160> NUMBER OF SEQ ID NOS: 6

<210> SEQ ID NO 1
<211> LENGTH: 17
<212> TYPE: DNA
<213> ORGANISM: Artificial
<220> FEATURE:
<223> OTHER INFORMATION: Primer

<400> SEQUENCE: 1
attaaccctc actaaag                                                  17

<210> SEQ ID NO 2
<211> LENGTH: 17
<212> TYPE: DNA
<213> ORGANISM: Artificial
<220> FEATURE:
<223> OTHER INFORMATION: Primer

<400> SEQUENCE: 2
tctgctcggc ctgttcc                                                  17

<210> SEQ ID NO 3
<211> LENGTH: 14
<212> TYPE: DNA
<213> ORGANISM: Artificial
<220> FEATURE:
<223> OTHER INFORMATION: Primer

<400> SEQUENCE: 3
tacatctaga taat                                                     14

<210> SEQ ID NO 4
<211> LENGTH: 13
<212> TYPE: DNA
<213> ORGANISM: Artificial
<220> FEATURE:
<223> OTHER INFORMATION: Primer

<400> SEQUENCE: 4
ttatctagat gta                                                      13

<210> SEQ ID NO 5
<211> LENGTH: 21
<212> TYPE: DNA
<213> ORGANISM: Artificial
<220> FEATURE:
<223> OTHER INFORMATION: Primer

<400> SEQUENCE: 5

-continued tcgagtcaaa tacgtagtcg t                                21

<210> SEQ ID NO 6
<211> LENGTH: 21
<212> TYPE: DNA
<213> ORGANISM: Artificial
<220> FEATURE:
<223> OTHER INFORMATION: Primer

<400> SEQUENCE: 6
tgtttccgga ggaatttgca a                                21